(12) United States Patent
Low

(10) Patent No.: US 11,696,724 B2
(45) Date of Patent: Jul. 11, 2023

(54) METHODS OF IDENTIFYING SLEEP AND WAKING PATTERNS AND USES

(71) Applicant: Neurovigil, Inc., Moffett Field, CA (US)

(72) Inventor: Philip S. Low, Moffett Field, CA (US)

(73) Assignee: NEUROVIGIL, INC., Moffett Field, CA (US)

( * ) Notice: Subject to any disclaimer, the term of this patent is extended or adjusted under 35 U.S.C. 154(b) by 236 days.

(21) Appl. No.: 16/442,337

(22) Filed: Jun. 14, 2019

(65) Prior Publication Data

US 2020/0138366 A1 May 7, 2020

Related U.S. Application Data

(63) Continuation-in-part of application No. 13/129,185, filed as application No. PCT/US2009/064632 on Nov. 16, 2009, now abandoned.

(60) Provisional application No. 61/115,464, filed on Nov. 17, 2008, provisional application No. 61/114,986, filed on Nov. 14, 2008, provisional application No. 61/114,997, filed on Nov. 14, 2008.

(51) Int. Cl.
*A61B 5/00* (2006.01)
*A61B 5/316* (2021.01)
*A61B 5/369* (2021.01)
*A61B 5/374* (2021.01)

(52) U.S. Cl.
CPC ............ *A61B 5/4812* (2013.01); *A61B 5/316* (2021.01); *A61B 5/369* (2021.01); *A61B 5/374* (2021.01); *A61B 5/4848* (2013.01)

(58) Field of Classification Search
None
See application file for complete search history.

(56) References Cited

U.S. PATENT DOCUMENTS

| 5,626,145 A | 5/1997 | Clapp et al. | |
| 6,993,380 B1 * | 1/2006 | Modarres | A61B 5/4806 600/544 |
| 7,593,767 B1 * | 9/2009 | Modarres | A61B 5/4818 600/544 |
| 7,860,561 B1 * | 12/2010 | Modarres | A61B 5/4809 600/544 |
| 2003/0032893 A1 | 2/2003 | Koch | |

(Continued)

FOREIGN PATENT DOCUMENTS

KR 10-2003-0002677 A 1/2003
KR 10-2007-0109044 A 11/2007

(Continued)

OTHER PUBLICATIONS

Low, "A New Way To Look At Sleep: Separation & Convergence". University of California, San Diego. 2007 (Year: 2007).*

(Continued)

*Primary Examiner* — Michael R Bloch
(74) *Attorney, Agent, or Firm* — Kilpatrick Townsend & Stockton LLP

(57) ABSTRACT

Traditional analysis of sleep patterns requires several channel of data. This analysis can be useful for customized analysis including assessing sleep quality, detecting pathological conditions, determining the effect of medication on sleep states and identifying biomarkers, and drug dosages or reactions.

23 Claims, 46 Drawing Sheets

(56) References Cited

U.S. PATENT DOCUMENTS

| | | | |
|---|---|---|---|
| 2004/0073129 A1* | 4/2004 | Caldwell | A61B 5/6814 600/544 |
| 2004/0193068 A1* | 9/2004 | Burton | A61B 5/4812 600/544 |
| 2006/0293608 A1 | 12/2006 | Rothman et al. | |
| 2007/0016095 A1* | 1/2007 | Low | A61B 5/374 600/544 |
| 2007/0105180 A1 | 5/2007 | Shaw et al. | |
| 2007/0208269 A1 | 9/2007 | Mumford et al. | |
| 2007/0249952 A1* | 10/2007 | Rubin | A61B 5/4812 600/544 |
| 2008/0009685 A1* | 1/2008 | Kim | A61B 5/4815 600/300 |
| 2008/0071326 A1 | 3/2008 | Heruth et al. | |
| 2008/0127978 A1* | 6/2008 | Rubin | A61B 5/369 128/204.23 |
| 2008/0154111 A1 | 6/2008 | Wu et al. | |
| 2009/0253996 A1* | 10/2009 | Lee | A61B 5/16 600/544 |

FOREIGN PATENT DOCUMENTS

| | | |
|---|---|---|
| KR | 10-2008-0025673 A | 3/2008 |
| WO | 2005/018737 A1 | 3/2005 |
| WO | 2006/008743 A2 | 1/2006 |
| WO | 2006/122201 A2 | 11/2006 |
| WO | 2007/109745 A2 | 9/2007 |

OTHER PUBLICATIONS

Anderer et al., "An E-Health Solution for Automatic Sleep Classification according to Rechtschaffen and Kales: Validation Study of the Somnolyzer 24*7 Utilizing the Siesta Database", Neuropsychobiology, vol. 51, 2005, pp. 115-133.
Chediak et al., "How Many Polysomnograms Must Sleep Fellows Score Before Becoming Proficient at Scoring Sleep?", Journal of Clinical Sleep Medicine, vol. 2, No. 4, 2006, pp. 427-430.
Danker-Hopfe et al., "Interrater reliability between scorers from eight European sleep laboratories in subjects with different sleep disorders", J. Sleep. Res., vol. 13, 2000, pp. 63-69.
Destexhe et al., "Spatiotemporal Analysis of Local Field Potentials and Unit Discharges in Cat Cerebral Cortex during Natural Wake and Sleep States", The Journal of Neuroscience, vol. 19, No. 11, 1999, pp. 4595-4608.
Flexer et al., "A reliable probabilistic sleep stager based on a single EEG signal", Artif. Intell. Med., vol. 33, 2005, 26 pages.
Gervasoni et al., "Global Forebrain Dynamics Predict Rat Behavioral States and Their Transitions", The Journal of Neuroscience, vol. 24, No. 49, Dec. 8, 2004, pp. 11137-11147.
Gottesmann, Claude, "The Transition from Slow-wave Sleep to Paradoxical Sleep: Evolving Facts and Concepts of the Neurophysiological Processes Underlying the Intermediate Stage of Sleep", Neuroscience and Biobehavioral Reviews, vol. 20, No. 3, 1996, pp. 367-387.
Himanen et al., "Limitations of Rechtschaffen and Kales", Sleep Med. Rev., vol. 4, No. 2, 2000, pp. 149-167.
Kelley et al., "Reliability of rapid clinical staging of all night sleep EEG", Clin, Electroencephalography, vol. 16, No. 1, 1985, pp. 16-20.
Llinas et al., "Coherent 40-Hz oscillation characterizes dream state in humans", Proc. Natl. Acad. Sci. U S A., vol. 90, Mar. 1993, pp. 2078-2081.
Office Action received for Japanese Patent Application No. 2015-094583, dated Jun. 29, 2016,12 pages (6 pages of English Translation and 6 pages of Office Action).
Office Action received for Korean Patent Application No. 10-2011-4013607, dated Feb. 13, 2017, 7 pages (4 pages of English Translation and 3 pages of Office Action).
Roberts et al., "Analysis of the sleep EEG using a multilayer network with spatial organisation", IEE Proceedings—F vol. 139, No. 6, Dec. 1992, pp. 420-425.
Destexhe, et al.; "Thalamocortical Assemblies"; Oxford University Press; Monographs of the Physiological Society; vol. 49; 2001; pp. 347-391.
EP Extended Search Report received for corresponding EP Application No. 09826930.1 dated Jun. 6, 2013; 10 pages.
PCT IPRP received for corresponding PCT Application No. PCT/US2009/064632 mailed Oct. 20, 2011; 10 pages.
PCT ISR received for corresponding PCT Application No. PCT/US2009/064632 mailed Oct. 3, 2011; 3 pages.
PCT WO received for corresponding PCT Application No. PCT/US2009/064632 mailed Oct. 3, 2011; 8 pages.
Communication pursuant to Article 94(3) EPC dated Feb. 29, 2016 as received in corresponding EP Application No. 09826930.1; 4 pages.
Communication pursuant to Article 94(3) EPC dated Jan. 12, 2017 as received in corresponding EP Application No. 09826930.1; 5 pages.
Communication pursuant to Article 94(3) EPC dated Jan. 26, 2015 as received in corresponding EP Application No. 09826930.1; 4 pages.
Communication pursuant to Article 94(3) EPC dated Apr. 7, 2014 as received in corresponding EP Application No. 09826930.1; 6 pages.

* cited by examiner

| TABLE S5 - TOP REM | | | | |
|---|---|---|---|---|
| | % REM | Number | Mean Duration (s) | Mean Separation (s) |
| VA | | | | |
| S_9 | 25.2101 | 25 | 33.6 | 109.0909 |
| S_10 | 36.036 | 23 | 48.2609 | 102.6316 |
| S_11 | 11.1732 | 21 | 30 | 87.5 |
| S_18 | 15.1351 | 21 | 35.7143 | 163.6364 |
| S_19 | 35.9551 | 46 | 33.2609 | 96.7742 |
| S_20 | 29.0657 | 53 | 43.5849 | 137.0455 |
| MPI | | | | |
| S_2a | 37.6471 | 63 | 44.2857 | 70.4348 |
| S_2b | 41.8251 | 68 | 46.7647 | 74.6809 |
| S_3a | 25.3086 | 25 | 44.4 | 169.4118 |
| S_3b | 22.7513 | 37 | 30 | 111.25 |
| S_4a | 24.2553 | 48 | 31.875 | 119.1176 |
| S_4b | 17.9724 | 33 | 29.0909 | 187.1429 |
| S_5a | 15.1685 | 21 | 30 | 312 |
| S_5b | 13.4503 | 20 | 28.5 | 266.6667 |
| S_6a | 17.1123 | 30 | 28 | 136.9565 |
| S_6b | 16.2679 | 32 | 27.1875 | 161.0526 |
| S_7a | 34.8958 | 54 | 31.1111 | 80.9091 |
| S_7b | 31.7647 | 51 | 42.3529 | 97.5 |
| S_8a | 25.2475 | 33 | 42.7273 | 140 |
| S_8b | 34.2723 | 49 | 37.3469 | 120 |
| S_9a | 30.1508 | 45 | 38 | 95.2941 |
| S_9b | 33.3333 | 39 | 42.3077 | 86.5385 |
| S_10a | 15.8621 | 21 | 31.4286 | 125 |
| S_10b | 32.2034 | 41 | 38.0488 | 102.8571 |
| S_11a | 29.3785 | 41 | 32.9268 | 104.4828 |
| S_11b | 29.3413 | 33 | 40 | 98.1818 |

FIG. 28

| TABLE S6 - Eye Movements | | | | | |
|---|---|---|---|---|---|
| | Tonic | Phasic | | | |
| | no eye mvmts | 0-25% | 25-50% | 50-75% | 75-100% |
| VA | | | | | |
| S_9 | 31.8182 | 34.2105 | 16.6667 | 15.7895 | 20 |

FIG. 29

| | | | | | |
|---|---|---|---|---|---|
| S_10 | 43.1818 | 35.0877 | 11.1111 | 0 | NaN |
| S_11 | 8.046 | 15.2941 | 0 | NaN | NaN |
| S_18 | 21.2766 | 16.092 | 9.375 | 5.5556 | 0 |
| S_19 | 38.8889 | 34.2857 | 26.6667 | 33.3333 | NaN |
| S_20 | 44.4444 | 26.5487 | 10.2564 | 14.2857 | 20 |

FIG. 29 (cont.)

| TABLE S7 - Frangmentation | | | | |
|---|---|---|---|---|
| | H_IS-1_REM | P_IS-1-REM | H_W-REM | P_W-REM |
| VA | | | | |
| S_9 | 1 | 689E-13 | 1 | 1.43E-29 |
| S_10 | 1 | 2.83E-02 | 1 | 6.91E-08 |
| S_11 | 1 | 0.0035 | 1 | 2.65E-02 |
| S_18 | 1 | 1.15E-12 | 1 | 1.88E-27 |
| S_19 | 1 | 6.27E-08 | 1 | 2.27E-17 |
| S_20 | 1 | 5.78E-11 | 1 | 7.53E-06 |
| | | | | |
| MPI | | | | |
| S_2a | 1 | 1.40E-04 | 1 | 0.0041 |
| S_2b | 0 | 0.2307 | 0 | 0.1047 |
| S_3a | 1 | 0.0054 | 1 | 1.62E-04 |
| S_3b | 1 | 5.41E-06 | 1 | 1.51E-07 |
| S_4a | 1 | 4.41E-06 | 1 | 5.94E-12 |
| S_4b | 1 | 9.02E-10 | 1 | 6.91E-19 |
| S_5a | 1 | 1.02E-04 | 1 | 4.99E-15 |
| S_5b | 1 | 2.11E-06 | 1 | 2.12E-20 |
| S_6a | 1 | 1.81E-07 | 1 | 7.93E- |

FIG. 30

|       |   |          |   | 28        |
|-------|---|----------|---|-----------|
| S_6b  | 1 | 5.97E-07 | 1 | 2.14E-20  |
| S_7a  | 0 | 0.1648   | 1 | 3.17E-02  |
| S_7b  | 1 | 1.84E-02 | 0 | 2.07E-01  |
| S_8a  | 1 | 1.18E-13 | 1 | 1.88E-19  |
| S_8b  | 1 | 1.17E-06 | 1 | 4.68E-12  |
| S_9a  | 1 | 5.40E-03 | 1 | 6.00E-07  |
| S_9b  | 0 | 0.8904   | 1 | 4.07E-04  |
| S_10a | 1 | 7.27E-16 | 1 | 9.06E-49  |
| S_10b | 1 | 1.04E-06 | 1 | 1.47E-11  |
| S_11a | 1 | 2.50E-03 | 1 | 5.75E-11  |
| S_11b | 1 | 8.12E-06 | 1 | 4.44E-04  |

FIG. 30
(cont.)

| Table S9 - Agreement Matrix - REM |||||||||
|---|---|---|---|---|---|---|---|---|
| VA - 9 | Automated || | Automated |||||
| Human | REM UP | REM DOWN | Human | SWS | IS | REM UP | REM DOWN | W |
| SWS-4 | 0 | 0 | REM UP | 0 | 10 | 90 | 0 | 0 |
| SWS-3 | 0 | 0 | REM DOWN | 0 | 11.236 | 0 | 88.764 | 0 |
| IS-2 | 12.5 | 1.2048 | | | | | | |
| IS-1 | 10.7143 | 1.2048 | | | | | | |
| REM UP | 48.2143 | 0 | | | | | | |
| REM DOWN | 0 | 95.1807 | | | | | | |
| W | 28.5714 | 2.4096 | | | | | | |
| M | 0 | 0 | | | | | | |
| VA - 10 | Automated || | Automated |||||
| Human | REM UP | REM DOWN | Human | SWS | IS | REM UP | REM DOWN | W |
| SWS-4 | 0 | 0 | REM UP | 0 | 27.5 | 72.5 | 0 | 0 |
| SWS-3 | 0 | 0 | REM DOWN | 0 | 5.6338 | 0 | 94.3662 | 0 |
| IS-2 | 14 | 15.8537 | | | | | | |
| IS-1 | 8 | 1.2195 | | | | | | |
| REM UP | 58 | 0 | | | | | | |
| REM DOWN | 0 | 81.7073 | | | | | | |
| W | 18 | 0 | | | | | | |
| M | 2 | 1.2195 | | | | | | |
| VA - 11 | Automated || | Automated |||||
| Human | REM UP | REM DOWN | Human | SWS | IS | REM UP | REM DOWN | W |
| SWS-4 | 0 | 0.3861 | REM UP | 0 | 0 | 100 | 0 | 0 |
| SWS-3 | 0 | 0 | REM DOWN | 0 | 0 | 0 | 100 | 0 |
| IS-2 | 74.4681 | 36.2934 | | | | | | |
| IS-1 | 3.1915 | 1.1583 | | | | | | |

FIG. 31

| | | |
|---|---|---|
| REM DOWN | 0 | 55.4054 |
| W | 7.0796 | 1.3514 |
| M | 1.7699 | 0.4505 |

| MPI - 10a | Automated | |
|---|---|---|
| Human | REM UP | REM DOWN |
| SWS-4 | 0 | 0 |
| SWS-3 | 0 | 0 |
| IS-2 | 7.0175 | 11.1111 |
| IS-1 | 12.2807 | 9.0278 |
| REM UP | 28.0702 | 0 |
| REM DOWN | 8.7719 | 77.0833 |
| W | 43.8596 | 2.7778 |
| M | 0 | 0.4329 |

| Human | Automated | | | | |
|---|---|---|---|---|---|
| | SWS | IS | REM UP | REM DOWN | W |
| REM UP | 0 | 30.4348 | 69.5652 | 0 | 0 |
| REM DOWN | 0 | 4.918 | 4.0984 | 90.9836 | 0 |

| MPI - 10b | Automated | |
|---|---|---|
| Human | REM UP | REM DOWN |
| SWS-4 | 0 | 0 |
| SWS-3 | 0 | 0 |
| IS-2 | 6.8966 | 2.8369 |
| IS-1 | 27.5862 | 15.6028 |
| REM UP | 50.5747 | 0 |
| REM DOWN | 0 | 79.4326 |
| W | 13.7931 | 1.4184 |
| M | 1.1494 | 0.7092 |

| Human | Automated | | | | |
|---|---|---|---|---|---|
| | SWS | IS | REM UP | REM DOWN | W |
| REM UP | 0 | 22.807 | 77.193 | 0 | 0 |
| REM DOWN | 0 | 6.6667 | 0 | 93.3333 | 0 |

| MPI - 11a | Automated |
|---|---|
| | Automated |

FIG. 31
(cont.)

| Human | REM UP | REM DOWN |
|---|---|---|
| SWS-4 | 0 | 0 |
| SWS-3 | 0 | 0 |
| IS-2 | 0 | 0 |
| IS-1 | 0 | 0 |
| REM UP | 0 | 0 |
| REM DOWN | 0 | 0 |
| W | 100 | 100 |
| M | 0 | 0 |

| Human | SWS | IS | REM UP | REM DOWN | W |
|---|---|---|---|---|---|
| REM UP | 0 | 0 | 100 | 0 | 0 |
| REM DOWN | 0 | 0 | 100 | 0 | 0 |

MPI - 11b

| | Automated | |
|---|---|---|
| Human | REM UP | REM DOWN |
| SWS-4 | 0 | 0 |
| SWS-3 | 0 | 0 |
| IS-2 | 53.4351 | 26.7974 |
| IS-1 | 7.6336 | 9.8039 |
| REM UP | 29.771 | 0 |
| REM DOWN | 6.1069 | 60.7843 |
| W | 2.2901 | 0.6536 |
| M | 0.7634 | 1.9608 |

| | Automated | | | | |
|---|---|---|---|---|---|
| Human | SWS | IS | REM UP | REM DOWN | W |
| REM UP | 0 | 20.4082 | 79.5918 | 0 | 0 |
| REM DOWN | 4.2373 | 10.1695 | 6.7797 | 78.8136 | 0 | average MPI

| | Automated | |
|---|---|---|
| Human | REM UP | REM DOWN |
| SWS-4 | 0 | 0 |
| SWS-3 | 0.036088 | 0 |

| | Automated | | | | |
|---|---|---|---|---|---|
| Human | SWS | IS | REM UP | REM DOWN | W |
| REM UP | 0.1368 | 17.93772 | 81.60486 | 0.320624 | 0 |
| REM DOWN | 0.289541 | 4.880494 | 0.864212 | 93.96576 | 0 |

FIG. 31
(cont.)

| | | |
|---|---|---|
| IS-2 | 20.84774 | 15.64285 |
| IS-1 | 13.75117 | 8.083676 |
| REM UP | 52.63081 | 0.109418 |
| REM DOWN | 1.699447 | 74.7556 |
| W | 9.278641 | 0.933171 |
| M | 1.767118 | 0.475288 |

| MPI - 11b | Automated | |
|---|---|---|
| Human | REM UP | REM DOWN |
| SWS-4 | 0 | 0.016787 |
| SWS-3 | 0.026674 | 0 |
| IS-2 | 23.30741 | 15.37121 |
| IS-1 | 12.54071 | 6.719017 |
| REM UP | 50.51496 | 0.147765 |
| REM DOWN | 1.282765 | 75.91143 |
| W | 10.45998 | 1.104461 |
| M | 1.867504 | 0.72933 |

| | Automated | | | | |
|---|---|---|---|---|---|
| Human | SWS | IS | REM UP | REM DOWN | W |
| REM UP | 0.101113 | 15.59398 | 83.86089 | 0.444022 | 0 |
| REM DOWN | 0.214009 | 5.047843 | 0.676904 | 94.06125 | 0 |

FIG. 31
(cont.)

| | | | | | | | |
|---|---|---|---|---|---|---|---|
| REM UP | 21.2766 | 0 | | | | | |
| REM DOWN | 0 | 61.39 | | | | | |
| W | 0 | 0.3861 | | | | | |
| M | 1.0638 | 0.3861 | | | | | |
| | | | | | | | |
| VA - 18 | Automated | | | Automated | | | |
| Human | REM UP | REM DOWN | Human | SWS | IS | REM UP | REM DOWN | W |
| SWS-4 | 0 | 0 | REM UP | 0 | 27.5 | 72.5 | 0 | 0 |
| SWS-3 | 0 | 0 | REM DOWN | 0 | 5.6338 | 0 | 94.3662 | 0 |
| IS-2 | 34.0909 | 8.0925 | | | | | |
| IS-1 | 15.9091 | 1.2195 | | | | | |
| REM UP | 29.5455 | 0 | | | | | |
| REM DOWN | 0 | 76.8786 | | | | | |
| W | 17.0455 | 6.3584 | | | | | |
| M | 3.4091 | 2.3121 | | | | | |
| | | | | | | | |
| VA - 19 | Automated | | | Automated | | | |
| Human | REM UP | REM DOWN | Human | SWS | IS | REM UP | REM DOWN | W |
| SWS-4 | 0 | 0 | REM UP | 0 | 3.125 | 96.875 | 0 | 0 |
| SWS-3 | 0 | 0 | REM DOWN | 0 | 0 | 0.8772 | 99.1228 | 0 |
| IS-2 | 21.6 | 12.3188 | | | | | |
| IS-1 | 10.4 | 2.1739 | | | | | |
| REM UP | 49.6 | 0 | | | | | |
| REM DOWN | 0.8 | 81.8841 | | | | | |
| W | 16 | 0 | | | | | |
| M | 1.6 | 3.632 | | | | | |
| | | | | | | | |
| VA - 20 | Automated | | | Automated | | | |
| Human | REM UP | REM | Human | SWS | IS | REM UP | REM | W |

FIG. 31
(cont.)

| | | DOWN |
|---|---|---|
| SWS-4 | 0 | 0 |
| SWS-3 | 0 | 0 |
| IS-2 | 25 | 13.8462 |
| IS-1 | 6.4516 | 5 |
| REM UP | 60.4839 | 1.5385 |
| REM DOWN | 0 | 78.0769 |
| W | 3.2258 | 0.3846 |
| M | 4.8387 | 1.1538 |

| | | | | DOWN | |
|---|---|---|---|---|---|
| REM UP | 0 | 5.9524 | 89.2857 | 4.7619 | 0 |
| REM DOWN | 0 | 0.9756 | 0 | 99.0244 | 0 |

| Average VA | Automated | |
|---|---|---|
| Human | REM UP | REM DOWN |
| SWS-4 | 0 | 0.06435 |
| SWS-3 | 0 | 0 |
| IS-2 | 30.2765 | 14.60157 |
| IS-1 | 9.111083 | 2.852483 |
| REM UP | 44.52005 | 0.256417 |
| REM DOWN | 0.133333 | 79.18627 |
| W | 13.80712 | 1.589783 |
| M | 2.151933 | 1.449117 |

| | Automated | | | | |
|---|---|---|---|---|---|
| Human | SWS | IS | REM UP | REM DOWN | W |
| REM UP | 0 | 8.953383 | 90.25297 | 0.79365 | 0 |
| REM DOWN | 0 | 5.522 | 0.1462 | 94.3318 | 0 |

| MRI - 2a | Automated | |
|---|---|---|
| Human | REM UP | REM DOWN |
| SWS-4 | 0 | 0 |
| SWS-3 | 0.6135 | 0 |
| IS-2 | 27.6074 | 24.5536 |
| IS-1 | 11.0429 | 4.0179 |

| | Automated | | | | |
|---|---|---|---|---|---|
| Human | SWS | IS | REM UP | REM DOWN | W |
| REM UP | 0 | 1.0417 | 95.8333 | 3.125 | 0 |
| REM DOWN | 0 | 2.5157 | 0 | 97.4843 | 0 |

FIG. 31
(cont.)

| | | |
|---|---|---|
| REM UP | 56.4417 | 1.3393 |
| REM DOWN | 0 | 69.1964 |
| W | 3.681 | 0.4464 |
| M | 0.6135 | 0.4464 |

| MPI - 2b | Automated | |
|---|---|---|
| Human | REM UP | REM DOWN |
| SWS-4 | 0 | 0 |
| SWS-3 | 0 | 0 |
| IS-2 | 22.695 | 31.1688 |
| IS-1 | 6.383 | 5.6277 |
| REM UP | 67.3759 | 0 |
| REM DOWN | 0 | 60.6061 |
| W | 3.5461 | 2.1645 |
| M | 0 | 0.4329 |

| | Automated | | | | |
|---|---|---|---|---|---|
| Human | SWS | IS | REM UP | REM DOWN | W |
| REM UP | 0 | 13.6364 | 86.3636 | 0 | 0 |
| REM DOWN | 0 | 8.4967 | 0 | 91.5033 | 0 |

| MPI - 3a | Automated | |
|---|---|---|
| Human | REM UP | REM DOWN |
| SWS-4 | 0 | 0 |
| SWS-3 | 0 | 0 |
| IS-2 | 24 | 23.7288 |
| IS-1 | 22.6667 | 12.4294 |
| REM UP | 48 | 0 |
| REM DOWN | 0 | 62.7119 |
| W | 4 | 0.565 |
| M | 1.3333 | 0.565 |

| | Automated | | | | |
|---|---|---|---|---|---|
| Human | SWS | IS | REM UP | REM DOWN | W |
| REM UP | 0 | 12.1951 | 87.8049 | 0 | 0 |
| REM DOWN | 0 | 8.2645 | 0 | 91.7355 | 0 |

| MPI - 3b | Automated |
|---|---|

| | Automated |
|---|---|

FIG. 31
(cont.)

| Human | REM UP | REM DOWN |
|---|---|---|
| SWS-4 | 0 | 0 |
| SWS-3 | 0 | 0 |
| IS-2 | 25.6757 | 18.75 |
| IS-1 | 20.2703 | 7.8125 |
| REM UP | 48.6486 | 0.5208 |
| REM DOWN | 0 | 71.3542 |
| W | 2.7027 | 0.5208 |
| M | 2.7027 | 1.0417 |

| Human | SWS | IS | REM UP | REM DOWN | W |
|---|---|---|---|---|---|
| REM UP | 2.3256 | 11.6279 | 83.7209 | 2.3256 | 0 |
| REM DOWN | 0.6849 | 5.4795 | 0 | 93.8356 | 0 |

| MPI - 4a | Automated | |
|---|---|---|
| Human | REM UP | REM DOWN |
| SWS-4 | 0 | 0 |
| SWS-3 | 0 | 0 |
| IS-2 | 15.5556 | 10.5528 |
| IS-1 | 13.3333 | 4.0201 |
| REM UP | 62.2222 | 0 |
| REM DOWN | 1.1111 | 84.9246 |
| W | 3.3333 | 0 |
| M | 4.4444 | 0.5025 |

| | Automated | | | | |
|---|---|---|---|---|---|
| Human | SWS | IS | REM UP | REM DOWN | W |
| REM UP | 0 | 1.7544 | 98.2456 | 0 | 0 |
| REM DOWN | 0 | 4.4944 | 0.5618 | 94.9438 | 0 |

| MPI - 4b | Automated | |
|---|---|---|
| Human | REM UP | REM DOWN |
| SWS-4 | 0 | 0 |
| SWS-3 | 0 | 0 |
| IS-2 | 7.1429 | 6.7358 |
| IS-1 | 9.5238 | 1.0363 |

| | Automated | | | | |
|---|---|---|---|---|---|
| Human | SWS | IS | REM UP | REM DOWN | W |
| REM UP | 0 | 15.3846 | 84.6154 | 0 | 0 |
| REM DOWN | 0 | 1.1236 | 0 | 98.8764 | 0 |

FIG. 31
(cont.)

| | | |
|---|---|---|
| REM UP | 78.5714 | 0 |
| REM DOWN | 0 | 91.1917 |
| W | 2.381 | 0 |
| M | 2.381 | 1.0363 |

| MPI - 5a | Automated | |
|---|---|---|
| Human | REM UP | REM DOWN |
| SWS-4 | 0 | 0 |
| SWS-3 | 0 | 0 |
| IS-2 | 51.8519 | 9.0361 |
| IS-1 | 1.8519 | 2.4096 |
| REM UP | 38.889 | 0 |
| REM DOWN | 0 | 88.5542 |
| W | 3.7037 | 0 |
| M | 3.7037 | 0 |

| | Automated | | | | |
|---|---|---|---|---|---|
| Human | SWS | IS | REM UP | REM DOWN | W |
| REM UP | 0 | 22.2222 | 77.7778 | 0 | 0 |
| REM DOWN | 0 | 2.649 | 0 | 97.351 | 0 |

| MPI - 5b | Automated | |
|---|---|---|
| Human | REM UP | REM DOWN |
| SWS-4 | 0 | 0 |
| SWS-3 | 0 | 0 |
| IS-2 | 17.2414 | 14.7239 |
| IS-1 | 10.3448 | 2.454 |
| REM UP | 62.069 | 0 |
| REM DOWN | 3.4483 | 82.8221 |
| W | 6.8966 | 0 |
| M | 0 | 0 |

| | Automated | | | | |
|---|---|---|---|---|---|
| Human | SWS | IS | REM UP | REM DOWN | W |
| REM UP | 0 | 21.7391 | 78.2609 | 0 | 0 |
| REM DOWN | 0 | 8.1081 | 0.6757 | 91.2162 | 0 |

FIG. 31
(cont.)

| MPI - 6a | Automated | |
|---|---|---|
| Human | REM UP | REM DOWN |
| SWS-4 | 0 | 0 |
| SWS-3 | 0 | 0 |
| IS-2 | 8.5106 | 1.9737 |
| IS-1 | 2.1277 | 0 |
| REM UP | 46.8085 | 0 |
| REM DOWN | 4.2553 | 96.7105 |
| W | 38.2979 | 1.3158 |
| M | 0 | 0 |

| | Automated | | | | |
|---|---|---|---|---|---|
| Human | SWS | IS | REM UP | REM DOWN | W |
| REM UP | 0 | 31.25 | 68.75 | 0 | 0 |
| REM DOWN | 0 | 3.871 | 1.2903 | 94.8387 | 0 |

| MPI - 6b | Automated | |
|---|---|---|
| Human | REM UP | REM DOWN |
| SWS-4 | 0 | 0 |
| SWS-3 | 0 | 0 |
| IS-2 | 0 | 4.023 |
| IS-1 | 4 | 0.5747 |
| REM UP | 88 | 0 |
| REM DOWN | 4 | 94.8276 |
| W | 4 | 0.5747 |
| M | 0 | 0 |

| | Automated | | | | |
|---|---|---|---|---|---|
| Human | SWS | IS | REM UP | REM DOWN | W |
| REM UP | 0 | 35.2941 | 64.7059 | 0 | 0 |
| REM DOWN | 0 | 5.1429 | 0.5714 | 94.2857 | 0 |

| MPI - 7a | Automated | |
|---|---|---|
| Human | REM UP | REM DOWN |
| SWS-4 | 0 | 0 |
| SWS-3 | 0 | 0 |
| IS-2 | 25.5474 | 26.9565 |
| IS-1 | 24.0876 | 18.2609 |
| REM UP | 45.2555 | 0 |
| REM | 0 | 53.0435 |

| | Automated | | | | |
|---|---|---|---|---|---|
| Human | SWS | IS | REM UP | REM DOWN | W |
| REM UP | 0 | 7.4627 | 92.5373 | 0 | 0 |
| REM DOWN | 0 | 2.4 | 0 | 97.6 | 0 |

FIG. 31
(cont.)

| MPI - 7b (cont.) | Automated | | | Human | Automated | | | | |
|---|---|---|---|---|---|---|---|---|---|
| Human | REM UP | REM DOWN | | | SWS | IS | REM UP | REM DOWN | W |
| DOWN | | | | | | | | | |
| W | 2.9197 | 1.7391 | | | | | | | |
| M | 2.1898 | 0 | | | | | | | |

| MPI - 7b | Automated | | | Human | Automated | | | | |
|---|---|---|---|---|---|---|---|---|---|
| Human | REM UP | REM DOWN | | | SWS | IS | REM UP | REM DOWN | W |
| SWS-4 | 0 | 0 | | REM UP | 0 | 100 | 0 | 0 | 0 |
| SWS-3 | 0 | 0 | | REM DOWN | 0 | 100 | 0 | 0 | 0 |
| IS-2 | 90 | 80 | | | | | | | |
| IS-1 | 0 | 10 | | | | | | | |
| REM UP | 0 | 0 | | | | | | | |
| REM DOWN | 0 | 0 | | | | | | | |
| W | 0 | 0 | | | | | | | |
| M | 10 | 10 | | | | | | | |

| MPI - 8a | Automated | | | Human | Automated | | | | |
|---|---|---|---|---|---|---|---|---|---|
| Human | REM UP | REM DOWN | | | SWS | IS | REM UP | REM DOWN | W |
| SWS-4 | 0 | 0 | | REM UP | 0 | 76.4706 | 23.5294 | 0 | 0 |
| SWS-3 | 0 | 0 | | REM DOWN | 0 | 39.7351 | 0.6623 | 59.6026 | 0 |
| IS-2 | 59.854 | 7.6923 | | | | | | | |
| IS-1 | 16.7883 | 4.8077 | | | | | | | |
| REM UP | 8.7591 | 0 | | | | | | | |
| REM DOWN | 0.7299 | 86.5385 | | | | | | | |
| W | 12.4088 | 0.9615 | | | | | | | |
| M | 1.4599 | 0 | | | | | | | |

| MPI - 8b | Automated | | | Human | Automated | | | | |
|---|---|---|---|---|---|---|---|---|---|
| Human | REM UP | REM | | | SWS | IS | REM UP | REM | W |

FIG. 31 (cont.)

| Human | REM UP | REM DOWN |
|---|---|---|
| SWS-4 | 0 | 0 |
| SWS-3 | 0 | 0 |
| IS-2 | 26.2626 | 18.0723 |
| IS-1 | 13.1313 | 4.2169 |
| REM UP | 44.4444 | 0 |
| REM DOWN | 1.0101 | 77.7108 |
| W | 7.0707 | 0 |
| M | 8.0808 | 0 |

| Human | SWS | IS | REM UP | REM DOWN | W |
|---|---|---|---|---|---|
| REM UP | 0 | 39.726 | 60.274 | 0 | 0 |
| REM DOWN | 0 | 7.1429 | 0.7143 | 92.1429 | 0 |

| MPI - 9a | Automated | |
|---|---|---|
| Human | REM UP | REM DOWN |
| SWS-4 | 0 | 0 |
| SWS-3 | 0 | 0 |
| IS-2 | 17.2727 | 18.6916 |
| IS-1 | 22.7273 | 13.5514 |
| REM UP | 50.9091 | 0 |
| REM DOWN | 0 | 64.486 |
| W | 8.1818 | 2.3364 |
| M | 0.9091 | 0.9346 |

| | Automated | | | | |
|---|---|---|---|---|---|
| Human | SWS | IS | REM UP | REM DOWN | W |
| REM UP | 0 | 6.6667 | 93.3333 | 0 | 0 |
| REM DOWN | 0 | 0.7194 | 0 | 99.2806 | 0 |

| MRI - 9b | Automated | |
|---|---|---|
| Human | REM UP | REM DOWN |
| SWS-4 | 0 | 0 |
| SWS-3 | 0 | 0 |
| IS-2 | 17.6991 | 16.2162 |
| IS-1 | 24.7788 | 26.5766 |
| REM UP | 48.6726 | 0 |

| | Automated | | | | |
|---|---|---|---|---|---|
| Human | SWS | IS | REM UP | REM DOWN | W |
| REM UP | 0 | 11.2903 | 88.7097 | 0 | 0 |
| REM DOWN | 0 | 0.8065 | 0 | 99.1935 | 0 |

FIG. 31
(cont.)

| Table S9 - Agreement Matrix - REM | Stage II | | | Spindles | | | K-complex | | |
|---|---|---|---|---|---|---|---|---|---|
| | events | TOP (%) | DOWN (%) | events | TOP (%) | DOWN (%) | events | TOP (%) | DOWN (%) |
| VA - 9 | 185 | 96.2162 | 3.7838 | 16 | 93.75 | 6.25 | 4 | 100 | 0 |
| VA - 10 | 550 | 33.6364 | 66.3636 | 34 | 55.8824 | 44.1176 | 10 | 50 | 50 |
| VA - 18 | 1123 | 66.4292 | 33.5708 | 126 | 76.1905 | 23.8095 | 12 | 66.6667 | 33.3333 |
| VA - 19 | 1290 | 61.0078 | 38.9922 | 27 | 74.0741 | 25.9259 | 3 | 100 | 0 |

FIG. 32

Table S12 - Nearest Neighbor Analysis

| | Maual | | | | | | | | | | | |
|---|---|---|---|---|---|---|---|---|---|---|---|---|
| | %0,TOP | %1,TOP | %2,TOP | %0,DOWN | %1,DOWN | %2,DOWN | %0,TOP | %1,TOP | %2,TOP | %0,DOWN | %1,DOWN | %2,DOWN |
| VA-9  | 12.5    | 62.5    | 25      | 36      | 24      | 40      | 52.9412 | 32.3529 | 14.7059 | 25      | 25      | 50      |
| VA-9  | 12.5    | 62.5    | 25      | 36      | 24      | 40      | 52.9412 | 32.3529 | 14.7059 | 25      | 25      | 50      |
| VA-10 | 36.6667 | 50      | 13.3333 | 53.1915 | 40.4255 | 6.383   | 37.1429 | 51.4286 | 11.4286 | 58.1818 | 36.3636 | 5.4545  |
| VA-10 | 42.8571 | 45.7143 | 11.4286 | 56.8627 | 37.2549 | 5.8824  | 37.1429 | 51.4286 | 11.4286 | 58.1818 | 36.3636 | 5.4545  |
| VA-11 | 20      | 60      | 20      | 67.7165 | 29.1339 | 3.1496  | 63.4146 | 31.7073 | 4.878   | 76.3889 | 21.2963 | 2.3148  |
| VA-11 | 33.3333 | 50      | 16.6667 | 70      | 27.1429 | 2.8571  | 63.4146 | 31.7073 | 4.878   | 76.3889 | 21.2963 | 2.3148  |
| VA-18 | 27.7778 | 61.1111 | 11.1111 | 48.1013 | 44.3038 | 7.5949  | 48.2143 | 46.4286 | 5.3571  | 57.1429 | 36.2637 | 6.534   |
| VA-18 | 38.0952 | 57.1429 | 4.7619  | 49.4118 | 43.5294 | 7.0588  | 54.386  | 42.1053 | 3.5088  | 58.0645 | 35.4839 | 6.4516  |
| VA-9  | 30      | 57.5    | 12.5    | 68.4932 | 28.7671 | 2.7397  | 52.9412 | 38.8235 | 8.2353  | 75.5556 | 2.2222  | 2.2222  |
| VA-9  | 28.9474 | 57.8947 | 13.1579 | 68.0556 | 29.1667 | 2.7778  | 52.9412 | 38.8235 | 8.2353  | 75.5556 | 2.2222  | 2.2222  |
| VA-20 | 55.3571 | 35.7143 | 8.9286  | 53.4653 | 33.6634 | 12.8713 | 61.6279 | 32.5581 | 5.814   | 64.6259 | 24.4898 | 10.8844 |
| VA-20 | 52      | 36      | 12      | 53.125  | 33.3333 | 13.5417 | 64.3678 | 29.8851 | 5.7471  | 64.1892 | 24.3243 | 11.4865 |

Drug side effect: the disappearance of Stage II sleep spindles.

METHODS OF IDENTIFYING SLEEP AND WAKING PATTERNS AND USES

CROSS-REFERENCE TO RELATED APPLICATIONS

This application is a continuation-in-part application of U.S. application Ser. No. 13/129,185 filed May 13, 2011, now pending; which is a 371 of PCT/US09/64632, filed Nov. 16, 2009; which is a claims the benefit of priority to U.S. Provisional Application Ser. No. 61/114,986, filed Nov. 14, 2008, and claims the benefit of priority to U.S. Provisional Application Ser. No. 61/114,997, filed on Nov. 14, 2008, and claims the benefit of priority to U.S. Provisional Application Ser. No. 61/115,464, filed on Nov. 17, 2008, which are incorporated herein in their entirety.

BACKGROUND OF THE INVENTION

Field of the Invention

The invention is directed to a method of analysis to extract and assess data collected from animals, including humans, to determine patterns of sleep from which one can further identify biomarkers and diagnostic applications

Background Information

Animals, including humans, require sleep in order to function properly. Up to one third of our entire life is devoted to sleep. A lack of sleep has a detrimental effect on physiology as well as memory and motor skills. Even various diseases can be linked to sleep disorders such as depression, Alzheimer's and kidney disease. The diagnosis of a sleep disorder typically results from the analysis of raw data collected for brain activity, muscle activity and other factors while patients are confined to a sleep laboratory with their head and body covered in electrodes. Often, the results differ greatly depending on the individual analyzing the data.

Electroencephalogram (EEG) is a tool used to measure electrical activity produced by the brain. The functional activity of the brain is collected by electrodes placed on the scalp. The EEG supplies important information about the brain function of a patient. Scalp EEG is thought to measure the aggregate of currents present post-synapse in the extracellular space resulting from the flow of ions out of or into dendrites that have been bound by neurotransmitters. EEG is mainly used in neurology as a diagnostic tool for epilepsy but the technique can be used in the study of other pathologies, including sleep disorders. Sleep recordings traditionally require multiple channels of data, including EEG.

In 1937, a taxonomy of human sleep was devised. This 5 stage taxonomy did not include Rapid Eye Movement (REM) sleep which was discovered in 1953. Five years later, Dement and Kleitman provided a description of sleep encompassing REM sleep and 4 non-REM (NREM) stages. In 1968, a committee led by Rechtschaffen and Kales devised "A Manual of Standardized terminology, Techniques and Scoring System for Sleep Stages of Human Subject" (R-K) which provided continuity with the prior description of sleep stages established by Dement and Kleitman. R-K classifies human sleep into two Slow Wave Sleep (SWS) stages (Stages III and IV), two Intermediate Sleep stages (Stages I and II) and REM sleep. In this classification, SWS EEG is composed of moderate to large amounts of high amplitude, slow wave activity; REM displays relatively low voltage, mixed frequency EEG in conjunction with episodic REMs (Rapid Eye Movements) and low-amplitude electromyogram (EMG); Intermediate Sleep (IS) has a relatively low voltage, mixed frequency EEG with stage II further displaying 12-14 Hz spindle oscillations and brief high amplitude K-complexes; Wakefulness (W) EEG contains alpha activity and/or low voltage, mixed frequency activity. This characterization of sleep and waking stages has been highly influential in guiding sleep research. Recently, rules provided by R-K were amended and the stages III/IV distinction was removed, leaving 3 NREM stages. While it is expected that sleep scorers will adapt to the new system, the precise number of sleep stages is still very much a topic of discussion.

REM sleep is often characterized by a period of rapid eye movements. REM has also been described as being tonic and phasic, in that during the tonic part of the REM sleep there were fewer or no eye movements. The phasic part of REM consisted of many eye movements. REM sleep has also been called, "paradoxical" because while the body and a brain are asleep, the raw EEG shows patterns similar to the brain of a person that is awake.

Given the variability of sleep structure both across and within individuals as well as the subjective nature of human scoring, it has been difficult to objectively segment a night of sleep into distinct stages based on a "fixed" interpretation of R-K; nor have techniques such as supervised and unsupervised classifiers been successful at automatic sleep stage classification across multiple data sets using a single channel of either human or animal brain activity. (Himanen, S. & Hasan, J., *Sleep Med. Rev.* 4, 149 (2000); Kelly, J., et al., *Clin. Electroenceph.* 16, 16 (1985); H. Danker-Hopfe, et al., *J Sleep Res.* 13, 63 (2004); Chediak, A., et al., *J. Clin Sleep Med.* 2, 427 (2006); Roberts, S. & Tarrassenko, L., *IEE Proceedings-F* 139, 420 (1992); Gervasoni, D., et al., *J. Neurosci.* 24, 11137 (2004); Anderer, P., et al., *Neuropsychobiology* 51, 115 (2005); Flexer, A., et al., *Artif Intell Med.* 33, 199 (2005)).

The further the voltage field is from the skull, the more difficult it is for the EEG to detect the electrical activity. Because human EEG recordings are low-pass filtered by the skull, higher frequency signals detected in intracranial animals studies, such as the interdigitation of high and low frequencies during Up and Down SWS states or the gamma oscillation during REM are difficult to observe, but they have been detected using magnetic measurements. The scalp recordings of human EEGs have a poor spatial resolution. Thus it is not known whether human SWS and REM are spatially "synchronized" and "desynchronized", respectively, as suggested by animal studies. (Destexhe, A., et al., *Neurosci.* 19, 4595 (1999); Gottesmann, C, *Neurosci. Biobehay. Rev.* 20, 367 (1996); Llinas, R., U. Ribary, *Proc. Natl. Acad. Sci. USA* 90, 2078 (1993); Destexhe, A., & Sejnowski, T. J. "*Thalamocortical Assemblies*," Destexhe, A., & T. J. Sejnowski, Eds. (Oxford Univ. Press, Oxford, 2001) pp. 347-391.)

The study of sleep patterns has consistently been an important research topic. In order to prepare for human use, it is well known that rodents are commonly used in scientific and animal research. The research is conducted to determine the safety and efficacy of drugs as well as pathological conditions, genetic testing, cosmetic safety, vaccines, and surgical procedures. The systematic study of EEG in animals from rodents to birds to non-human primates has been hampered by the requirement for surgery. Implanting electrodes can cause stress, blood loss and fatigue in animals. Additionally, the difficulty of inserting electrodes requires highly trained staff. Therefore, a substantial need exists for automated sleep analysis methods that can detect subtle but statistically significant changes in brain activity in the absence of invasive techniques from a single channel of EEG. In humans, another need is utilizing new sleep patterns for biomarker and diagnostic applications.

SUMMARY OF THE INVENTION

In general, the present invention describes a novel analysis method for the extraction and analysis of attenuated rhythms collected from the scalp of animals based on the combination of single channel analysis methods for sleep and non-invasive recordings.

One aspect of the invention is a method for differentiating the phases of sleep such as REM (Rapid Eye Movement) and deep sleep using less data than conventional methods. A single channel of EEG was sufficient to decouple sleep and waking stages and these are clearly separable.

The present invention further generalizes beyond the C3-A1 EEG derivation to alternative derivations, including even a single channel of electrooculography (EOG).

Another aspect of the invention is a method for using an algorithm to detect previously unidentified frequency waves produced during sleep using only one or two electrodes placed on the scalp or head.

Another aspect of the invention is the existence of a discrete number of human sleep stages and refutes the belief that REM sleep is "awake-like" or "paradoxical." Although REM is known to exhibit theta, the clear REM/W separation as well as between other stages is not apparent by eye or by previous analysis from a single channel of human EEG. The bimodal temporal fragmentation pattern of REM sleep is also striking.

Also within the scope of the present invention is a method that can be used to diagnose diseases that have been linked to disordered sleep prior to the onset of serious symptoms.

The present invention further includes a method for studying the effects of drugs on sleep and wakefulness as well as the detection of drugs in the system based on the sleep and waking patterns.

Also within the scope of this present invention is the ability to identify and define signatures of sleep and waking patterns so precisely that a biomarker of the sleep and waking state results.

Finally, these methods presents a rapid, economic and quantitatively rigorous alternative to manually scored sleep staging in both clinical and comparative research and should find many new applications.

The embodiments explain using this information to determine sleep states automatically. Other applications are described which automatically assess sleep quality, pathological conditions, and medication effects. There applications in accordance with the disclosure will be apparent from the description and drawings, and from the claims.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated and constitute a part of the specification wherein.

activity. IS displayed spindle activity (12-15 Hz) as well as gamma (30-50 Hz) and high-gamma activity (>50 Hz). W displayed beta, low gamma and high gamma activity (>80 Hz). c-d respectively same as a-b, for a different subject.

Figure 17:
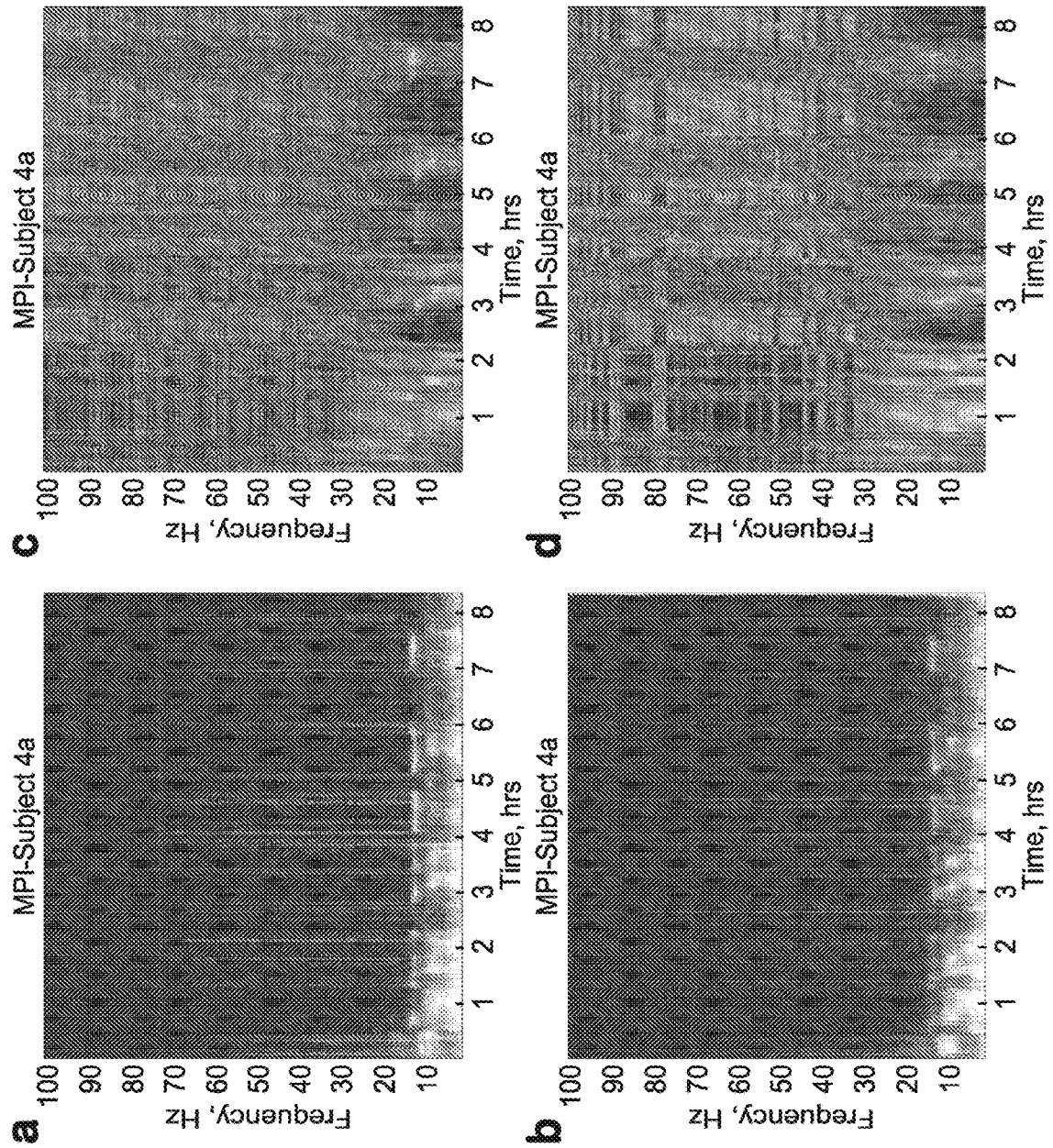
FIG. 17 details raw and normalized spectrograms Raw spectrogram data were calculated at 30 sec (a) or at a 3 sec spectral resolution over 1 sec increments (b). Each spectrogram was then normalized across time and frequency several times yielding a normalized spectrogram at 30 sec resolution (c) and another one at a 3 sec spectral resolution over 1 sec increments (d). While only movement artifacts have high frequency (>20 Hz) content in the raw data (a-b), the normalized spectrograms have much more high frequency activity (c-d).
Figure 18:
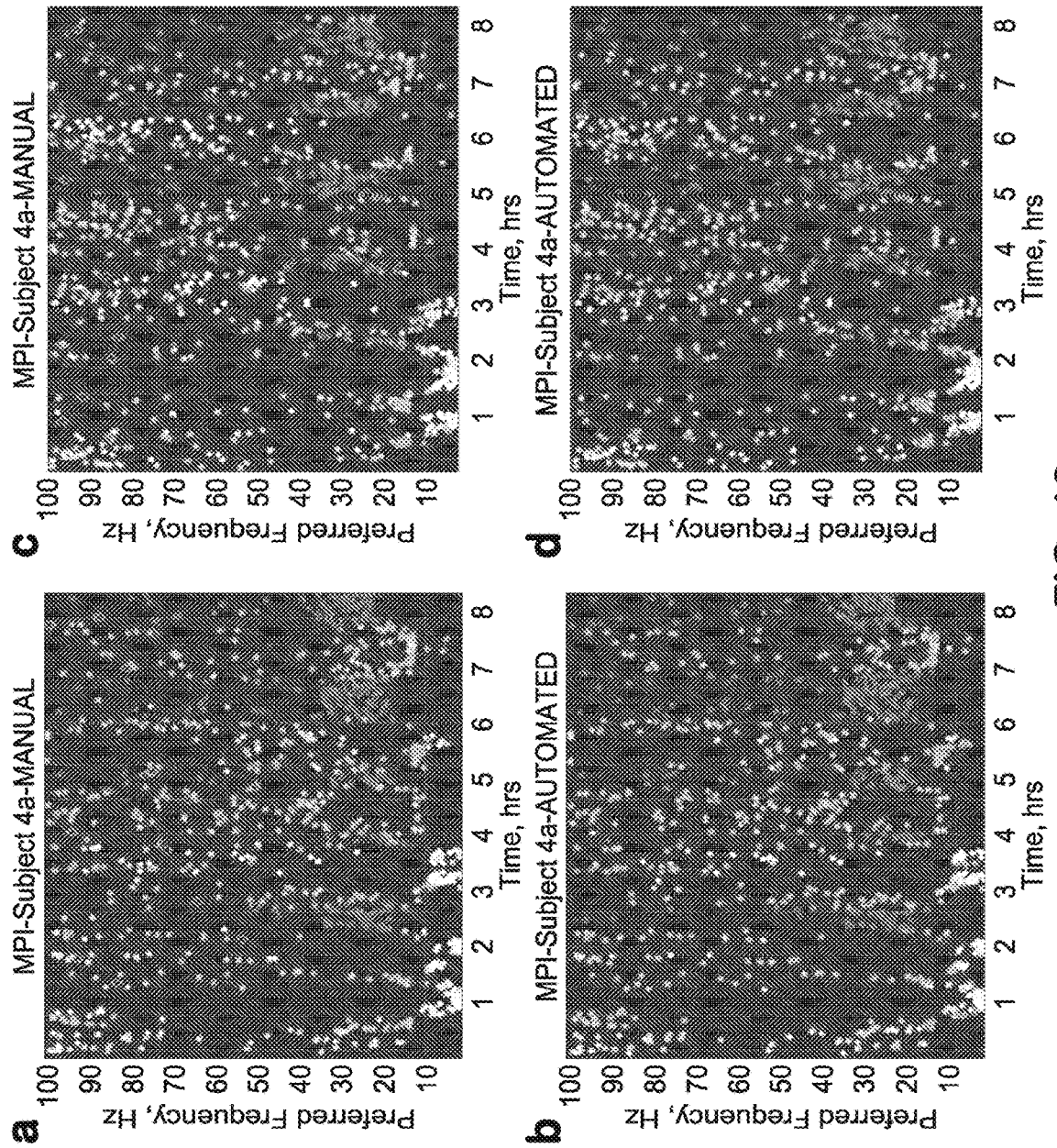
FIG. 18 depicts Preferred Frequency analysis over a spectrogram with multiple normalizations. The Preferred Frequency space was computed over the normalized spectrogram in FIG. 17 and labeled using both the manual (a) and automated (h) scoring. SWS was marked by low frequency (<10 Hz) activity. REM had beta and low gamma (20-40 Hz)
Figure 19:
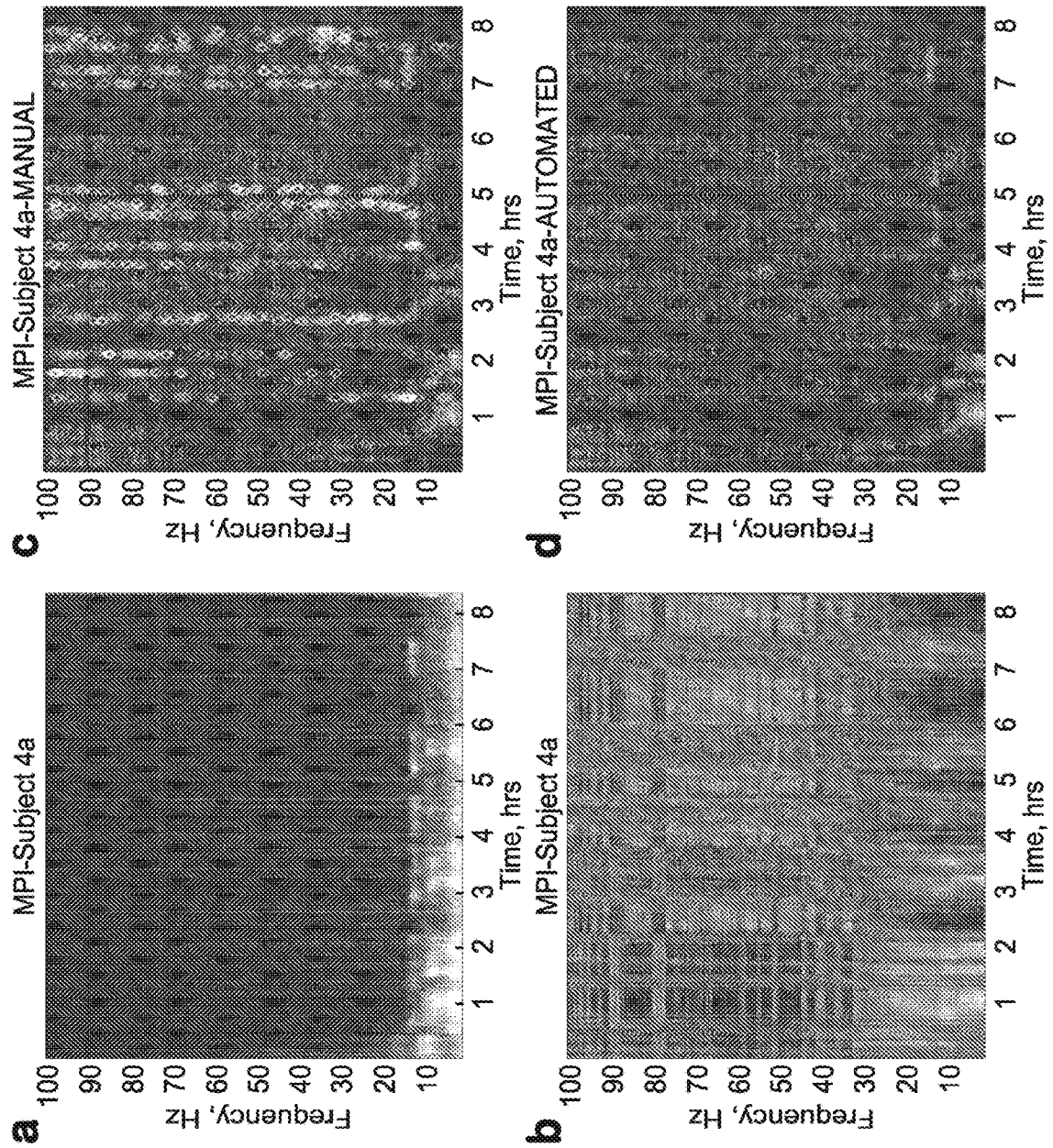

FIG. 19 details preferred frequency analysis over a spectrogram with multiple normalizations at high temporal resolution. FIG. 19a-b is identical to FIG. 17b-d, respectively. The analyses from FIGS. 18 a and b were respectively applied to a and b to yield c and d, respectively. The trends observed in FIG. 18 are reinforced at this temporal resolution. High-frequency information is also visible for SWS.

Figure 20:
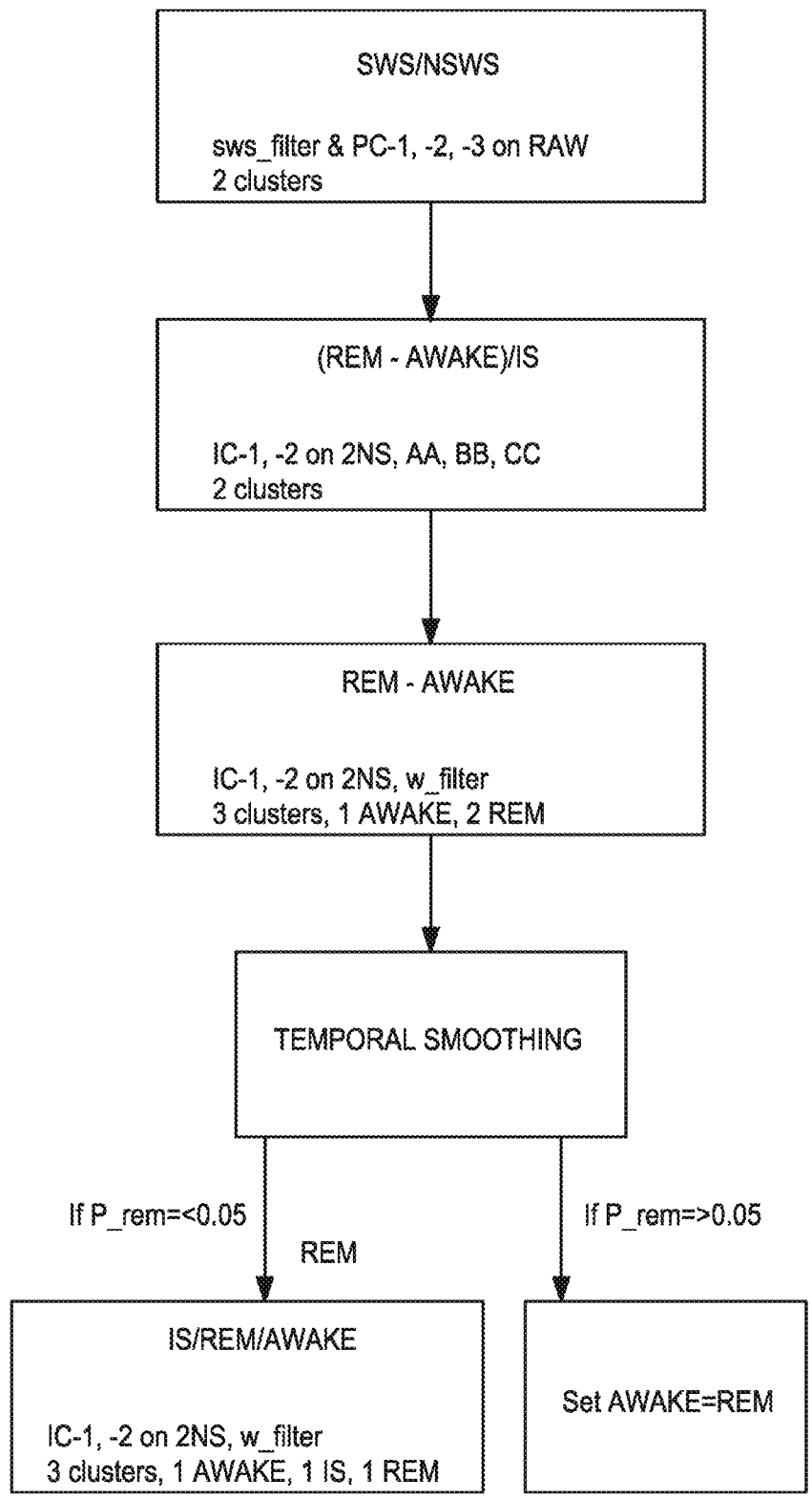

FIG. 20 depicts an algorithm flow chart. The algorithm serially identifies SWS, IS, REM and W using variables described in Materials and Methods. The data was then smoothed in time. The REM/W separation was measured again by computing a P value for the REM distribution. If the latter exceeds a fixed value, REM was rejected and replaced by W. If REM was accepted, it was split in W, REM and W. As a precaution, the REM-like events occurring at the very beginning of the night could be labeled as W. The increases in performance were minimal as REM and W tended to form different clusters. This is one algorithm that could be used:

The filters used in FIG. 20 are as follows.
sws_filter=mean(2NS(≤3 Hz));
w_filter=mean(2NS(9-12 Hz));
nrem_filter=mean(2NS(60-100 Hz))+mean(2NS(3-4 Hz))−[mean(2NS(12-14 Hz))+Fmean(2NS(25-60 Hz))+mean(2NS(15-25 Hz))]1;
AA=mean(2NS(12-14 Hz));
BB=mean(2NS(15-25 Hz));
CC=mean(WS(≤3 Hz));
DD=mean(2NS(9-12 HZ);
WS and 2NS correspond to the raw and doubly normalized spectrograms, respectively. The temporal fragmentation corresponds to the zscore of the mean of the absolute value of the temporal gradient of the spectrum normalized throughout time and frequency and was computed on a 1-100 Hz range unless otherwise noted.

Figure 21:
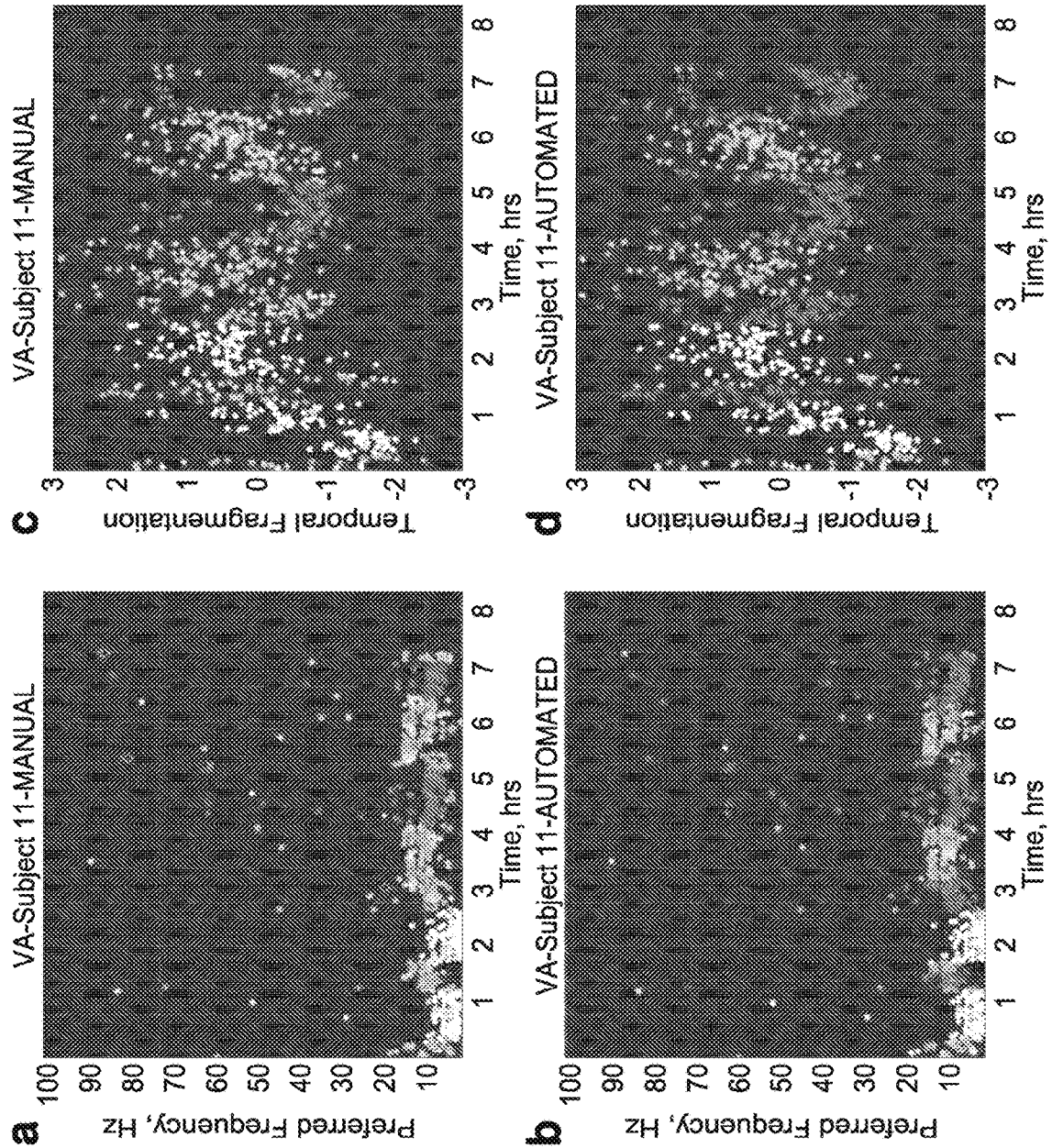

FIG. 21 depicts some discrepancies between automated and manual scoring. The overall agreement rate was 76.97% but half of the epochs scored by the human as IS (a, c, cyan) were found to be REM by the algorithm (b, d, red). These epochs had a signature closer to that of REM than IS in both the PFS (a-b) and the temporal fragmentation space (c-d), especially the second sets of epochs, occurring approximately after 2.5 hours of sleep. Reexamination of these epochs by the human scorer as well as by a second scorer did find traces of REM. Manual scores were left unchanged.

Figure 22:
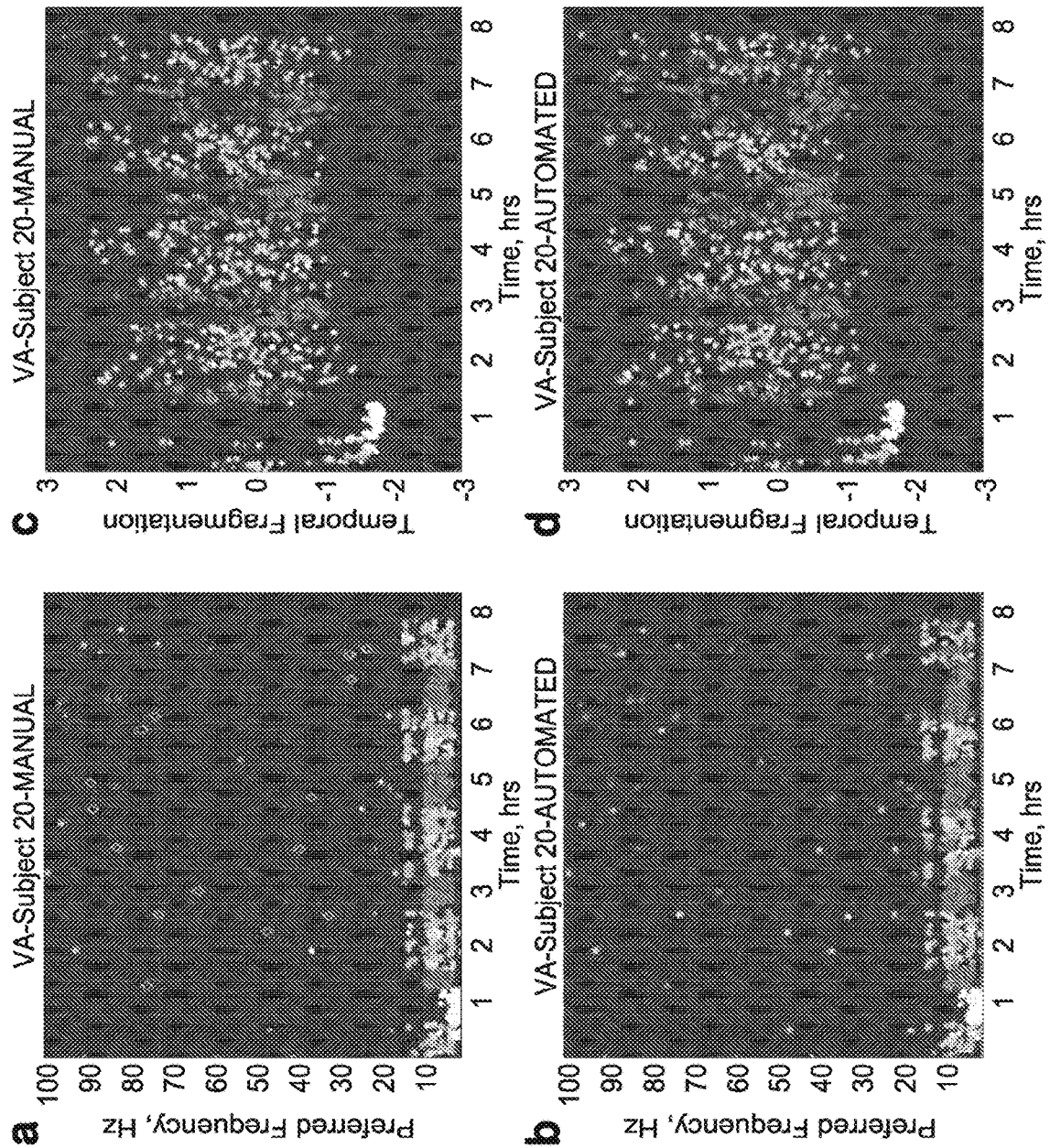

FIG. 22 depicts Preferred Frequency Space and Temporal Fragmentation. This display has a similar array to that depicted in FIG. 21. The overall agreement rate between automated and manual scoring for FIG. 18 is 83.8%.

Figure 23:
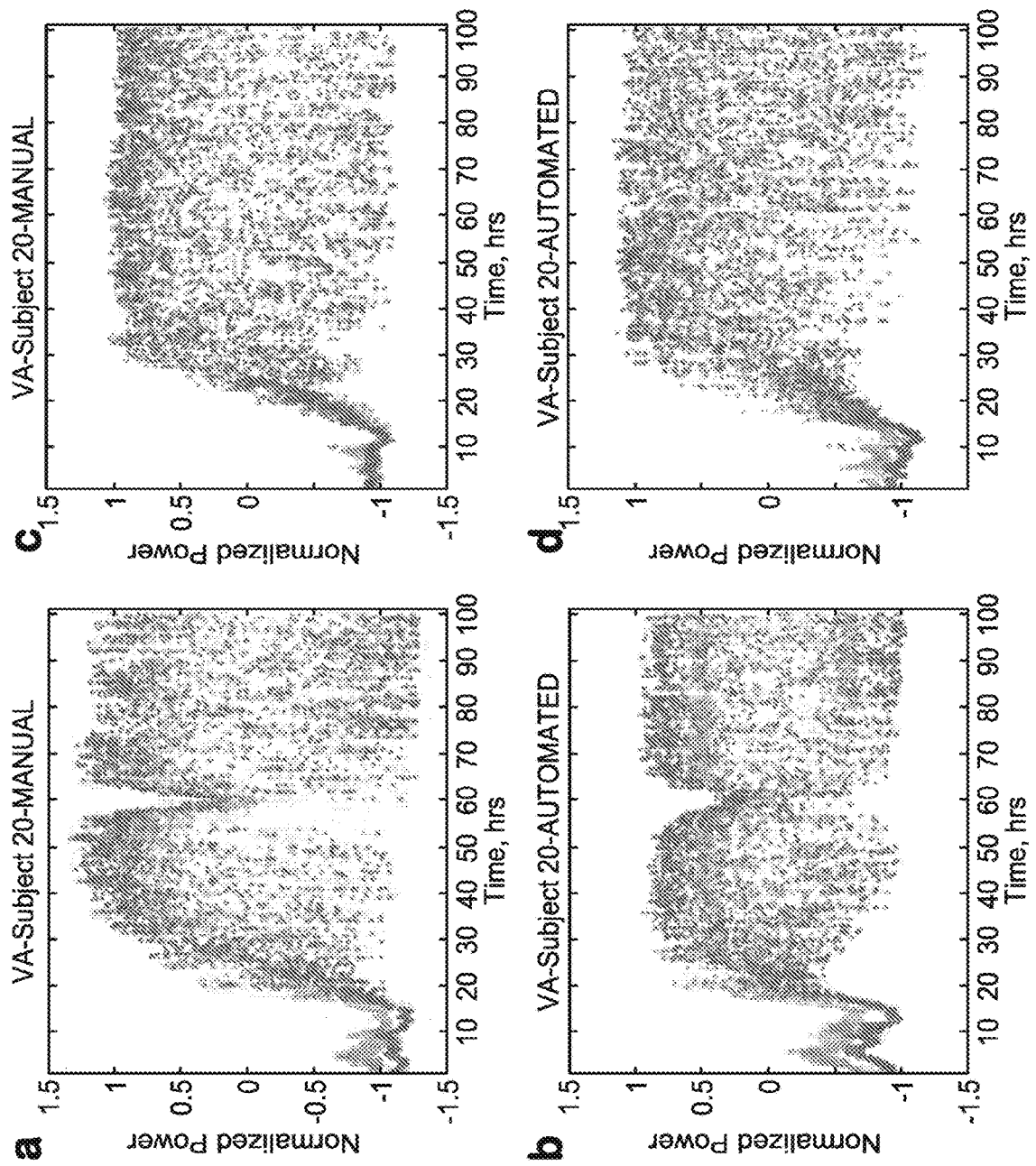

FIG. 23 represents spectra in the normalized space with iterated normalizations the spectrogram was normalized in time and frequency multiple times. REM sleep was manually scored. The stable and unstable components were isolated with a K-means clustering algorithm. The averages of the spectra for the stable (red) and unstable (green) components are shown in the space with multiple normalizations across time and frequency over multiple recordings (a-b UCSD VA Hospital (VA), c-d, Max-Planck Institute (MPI)). Note the elevated relative power at low frequencies for the unstable part of REM sleep as opposed to the stable part. The depression at 60 Hz is the VA data is most likely due to the use of a 60 Hz notch filter.

Figure 24:
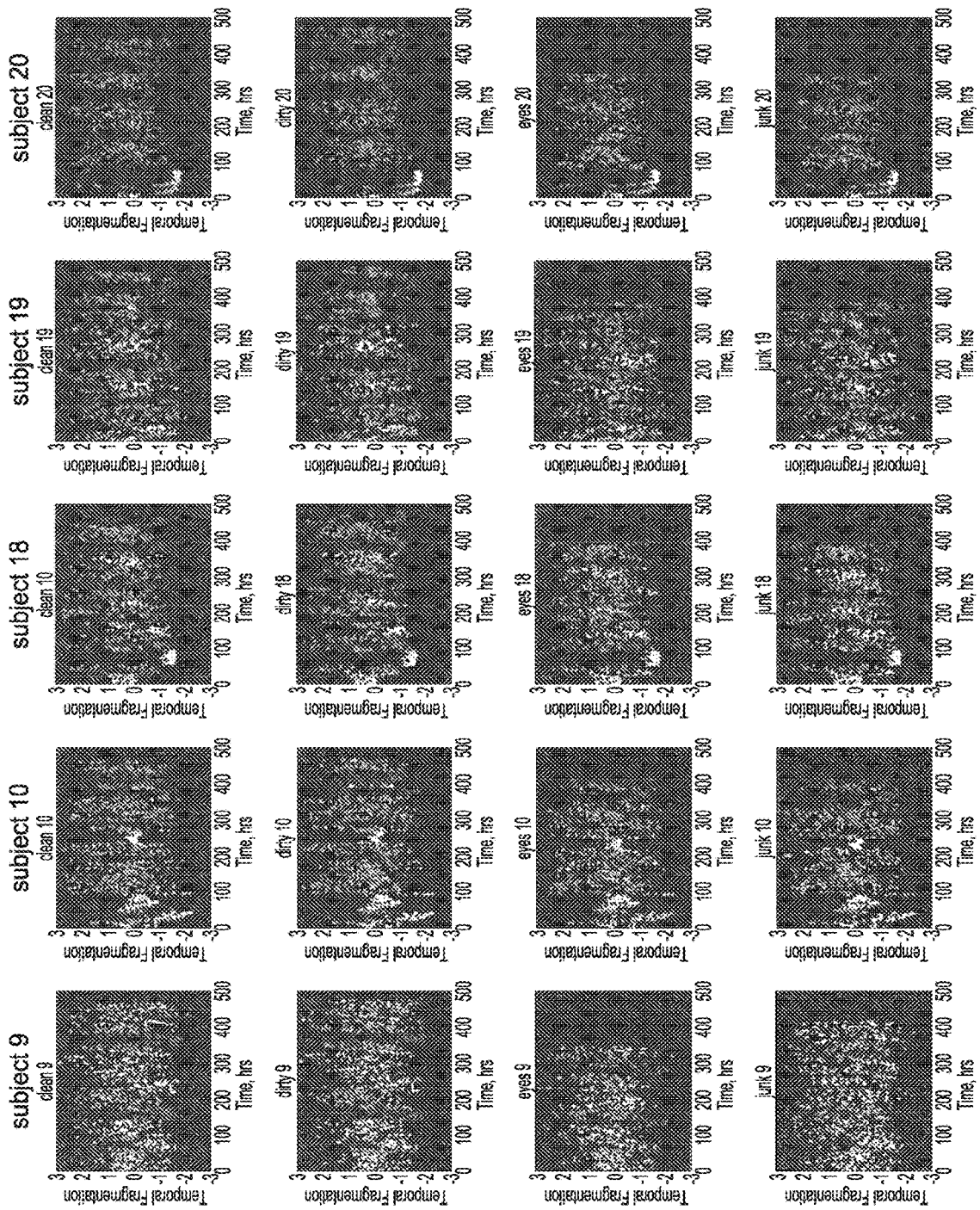

FIG. 24 depicts data gathered by subject. Every column corresponds to a different subject. The temporal fragmentation is plotted against time. The colors correspond to the sleep and wake states (red=REM, white=SWS, cyan=intermediate, yellow=awake). The rows are described as follows: the first row represents a removal of artifacts and REM landmarks from the raw data; the second row corresponds to the analysis on the full file; the third row corresponds to the analysis on only the eye movement artifacts for REM; and the fourth row corresponds to the analysis on only the landmarks and artifacts (excluding eye) for REM.

Figure 25:
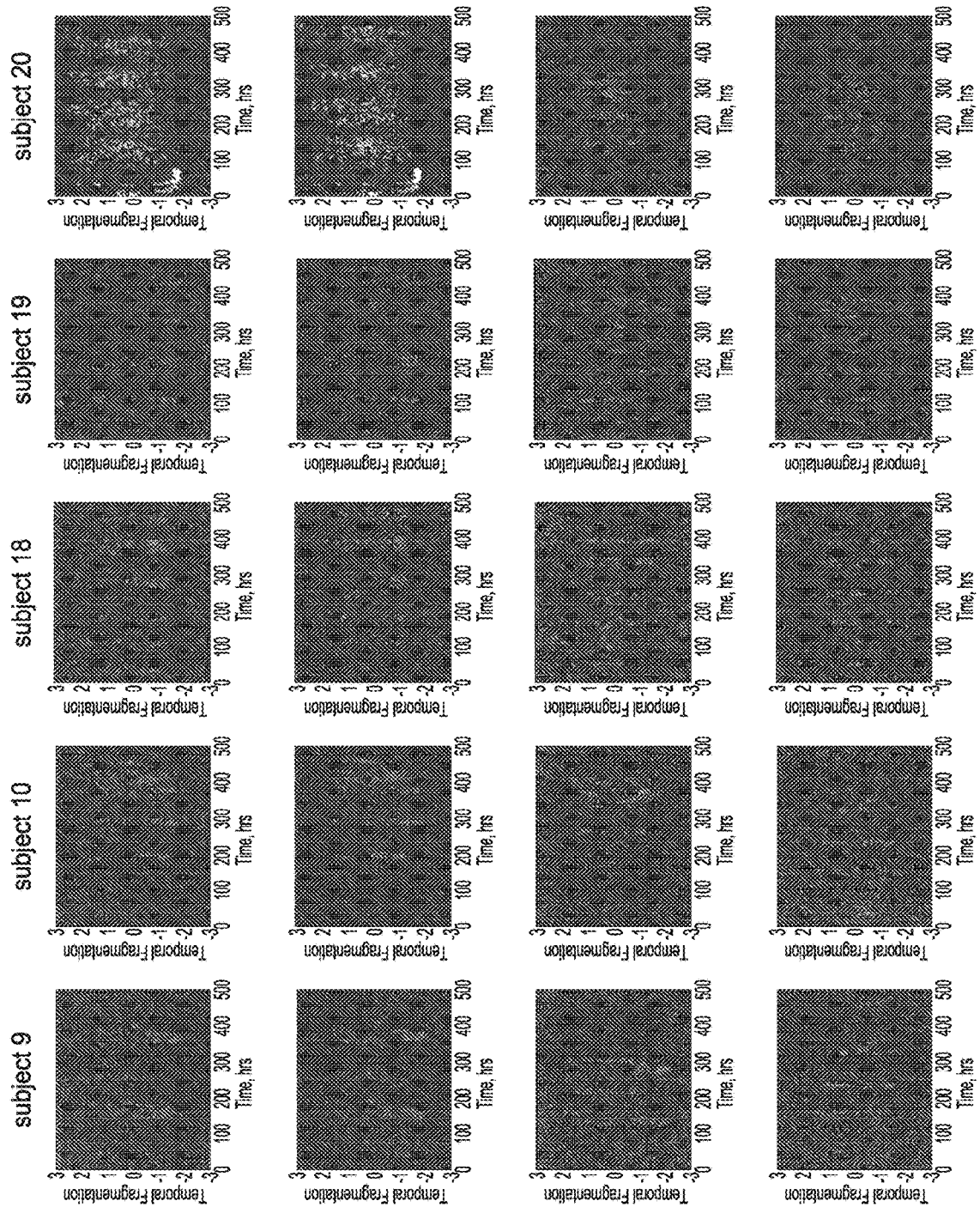

FIG. 25 represents plots on the data from FIG. 24, but only the REM data is graphed. A bimodal temporal fragmentation can be seen in row 1, despite the artifacts having been removed.

Figure 26:
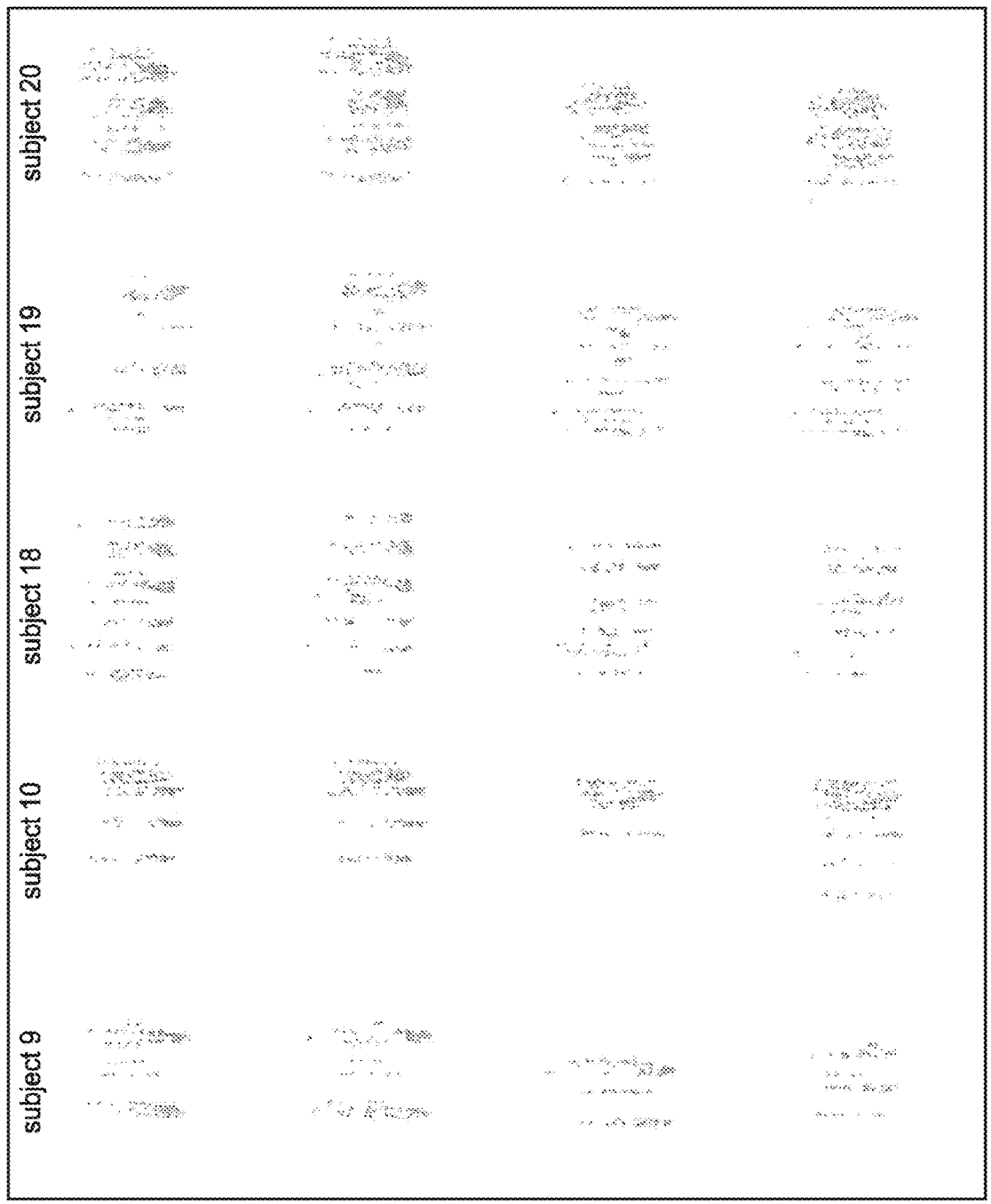

FIG. 26 represents the REM data from FIG. 25, with only the data points displayed.

Figure 27:
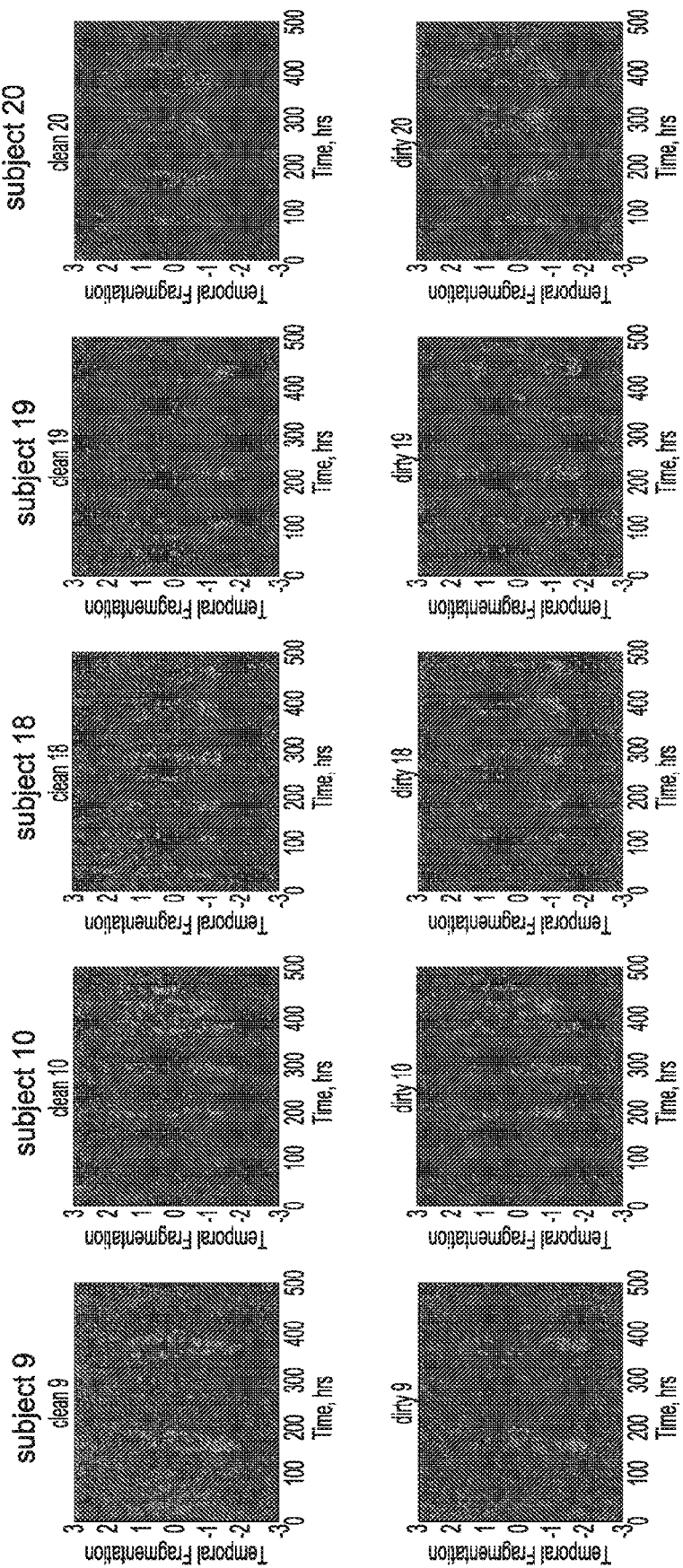

FIG. 27 depicts the first two rows from FIG. 25.

FIG. 28 is Table S5. This table depicts statistics on temporally fragmented part of REM sleep. The percentage of REM, number of episodes, their mean duration and separation is represented in each recording from both data sets.

FIG. 29 is Table S6. This table shows the fragmented and non-fragmented portions of REM sleep do not correspond to phasic or tonic REM. In the VA data only, REM was subdivided into epochs without eye movements (tonic REM) and epochs with 0-25%, 25-50%, 50-75%, 75-100% eye movements (phasic REM). For each subject, the percentage of times one of the substates listed above occurs in the unstable portion of REM is reported. Both tonic REM and phasic REM take place in the unstable part of REM.

FIG. 30 is Table S 7. This table illustrates that REM has a unique temporal fragmentation pattern which distinguishes it from Stage I and W. A KS analysis at a 30 second resolution as in Tables S2 and S3 is performed. The null hypothesis was rejected for REM versus Stage I (left columns) in 23 out 26 recordings and for REM vs. W (right columns) 24 out of 26 recordings, as defined by manual scoring.

FIG. 31 is Table S9, agreement matrices for REM components. For each subject, two matrices are presented. The matrices on the left and right should be read column-wise and row-wise, respectively. Each box in the left matrix corresponds to the percentage of times an epoch of the stage listed above as either the fragmented (REM UP) or stable (REM DOWN) components of REM as defined by the automated algorithm has been labeled as the stage on the left as defined by the human scorer. M corresponds to epochs labeled as movement. Each box in the right matrix corresponds to the percentage of time an epoch on the left, as defined by an automatic separation of manually identified REM is listed as the epoch above as defined by the algorithm. The REM UP/DOWN distinction is always done by a K-means algorithm on REM data, whether it is identified by the human scorer or the algorithm. Average percentage agreements were also computed for VA subjects, MPI subjects and both data sets, respectively. These matrices excluded three cases, where inspection of the preferred frequency map showed suspicious performance on the part of either the algorithm (MPI 7b and 11a) or the human scorer (MPI 8a). Most manually labeled REM components fell into the same automatically labeled REM components (right matrices). The unstable portion of REM as defined by the algorithm was most likely to be confused with stage II by the human when it is not scored as REM (left matrices).

FIG. 32 is Table S10. This table depicts REM outliers. On 4 VA subjects, 1 sec manually scored Stage II revealed that most of the spindles or K-complex, which were scored as REM by the algorithm did take place in the unstable part. The same was true for baseline stage II without spindles or K-complexes, in 3 out of 4 subjects (left columns, the exception being subject 10.

FIG. 33 is Table S12, a Nearest Neighbor analysis. Epochs devoid of artifacts were identified to establish whether proximity to an artifact could be responsible for the fragmented portion of REM. % XY means percentage of neighbors of Y (TOP or DOWN) composed of X (0=no artifact in either neighbor, 1=one neighbor is an artifact, 2=both neighbors are artifacts). As in the previous table, each row corresponds to a different scorer. Similarities and differences observed within results for subject 9, 18 and 20 are explained in the previous legend. Subjects 9 and 19 have respectively 18/34 and 45/85 epochs in the fragmented part of automatically identified REM which do not have any neighboring artifacts, leading to the same percentage in both cases.

Figure 34:
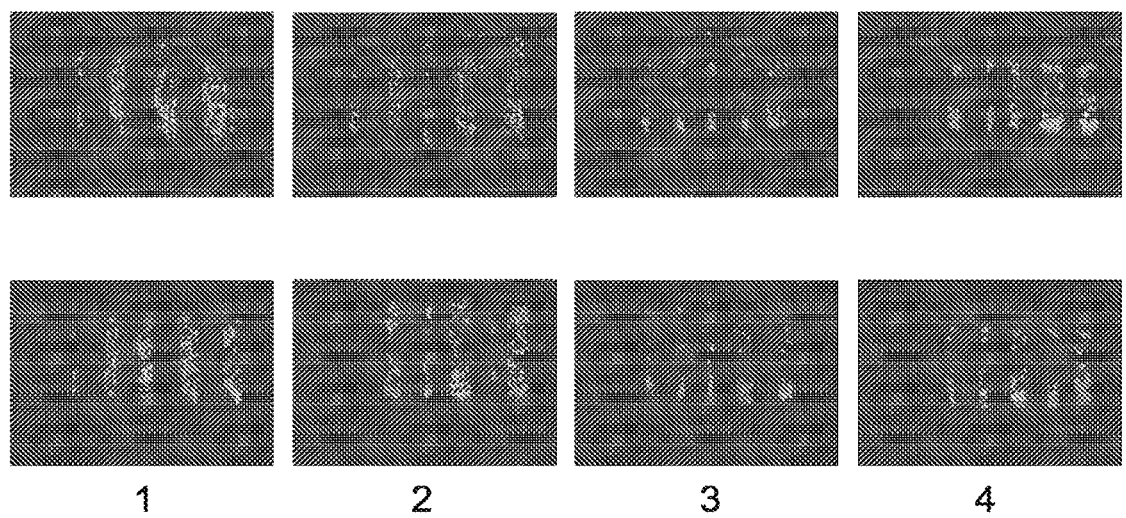

FIG. 34 represents the results of a study conducted on 4 pairs of twins. Each column in 1-4 corresponds to 4 pairs of twins (pair 1 is fraternal, pairs 2-4 is identical). Only REM is shown (temporal fragmentation across time). Twins exhibit a similar temporal fragmentation pattern.

Figure 35:
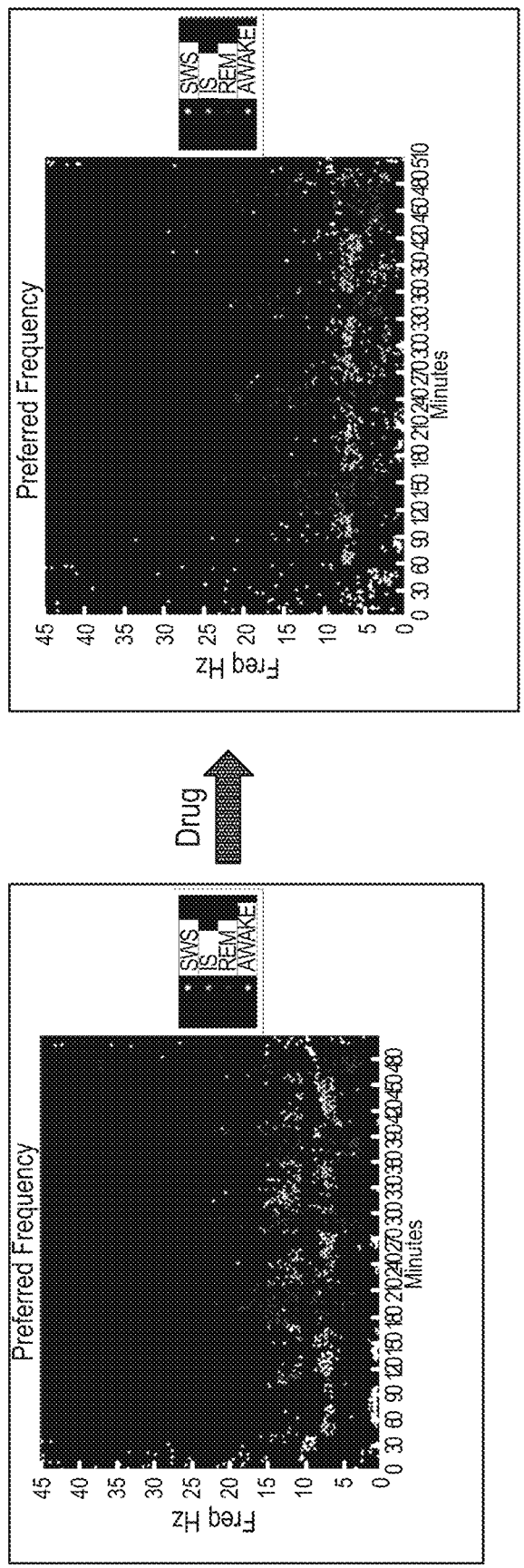

FIG. 35 depicts two Preferred Frequency plots, before and after administration of a drug to a subject.

DETAILED DESCRIPTION OF THE INVENTION

It is to be understood that the figures and descriptions of the present invention have been simplified to illustrate elements that are relevant for a clear understanding of the invention, while eliminating, for purpose of clarity, other elements that may be well known. The detailed description will be provided herein below with reference to the attached drawings.

The term "subject" in this application refers to both animals and humans.

The term "stable REM" refers visually to the bottom portion of the pattern as in the bimodal distribution of REM. The term "unstable REM" refers visually to the top portion of the pattern in the bimodal distribution of REM.

The methods described herein are disclosed in detail in PCT/US2006/018120, the disclosure is fully incorporated herein by reference.

The present invention provides a system and method to obtain and classify EEG data in both animals and humans. Obtained EEG signals are low-power frequency signals and follow a 1/f distribution, whereby the power in the signal is inversely related, e.g., inversely proportional, to the frequency.

EEG signals have typically been examined in time in series increments called epochs. For example, when the EEG signal is used for analyzing sleep, sleep may be segmented into one or more epochs to use for analysis. The epochs can be segmented into different sections using a scanning window, where the scanning window defines different sections of the time series increment. The scanning window can move via a sliding window, where sections of the sliding window have overlapping time series sequences. An epoch can alternatively span an entire time series, for example.

According to the present application, different forms of sleep state of a subject may be monitored. A sleep state is described as any distinguishable sleep or wakefulness that is representative of behavioral, physical or signal characteristics. Sleep states which are referred to in this application include slow wave sleep or SWS, rapid eye movement sleep or REM, intermediate sleep states also called inter or IS states, and awake states. Awake states may actually be part of the sleep state, and the awake states can be characterized by vigilance into attentiveness or levels of alertness. The intermediate sleep can also be characterized as intermediate-1 sleep and intermediate-2 sleep. An artifact may also be obtained during acquisition of an EEG. An artifact is data that misrepresents the EEG. For example, movement within a user that registers on the EEG may be an artifact. Example artifacts include muscle twitches and the like.

Figure 1:
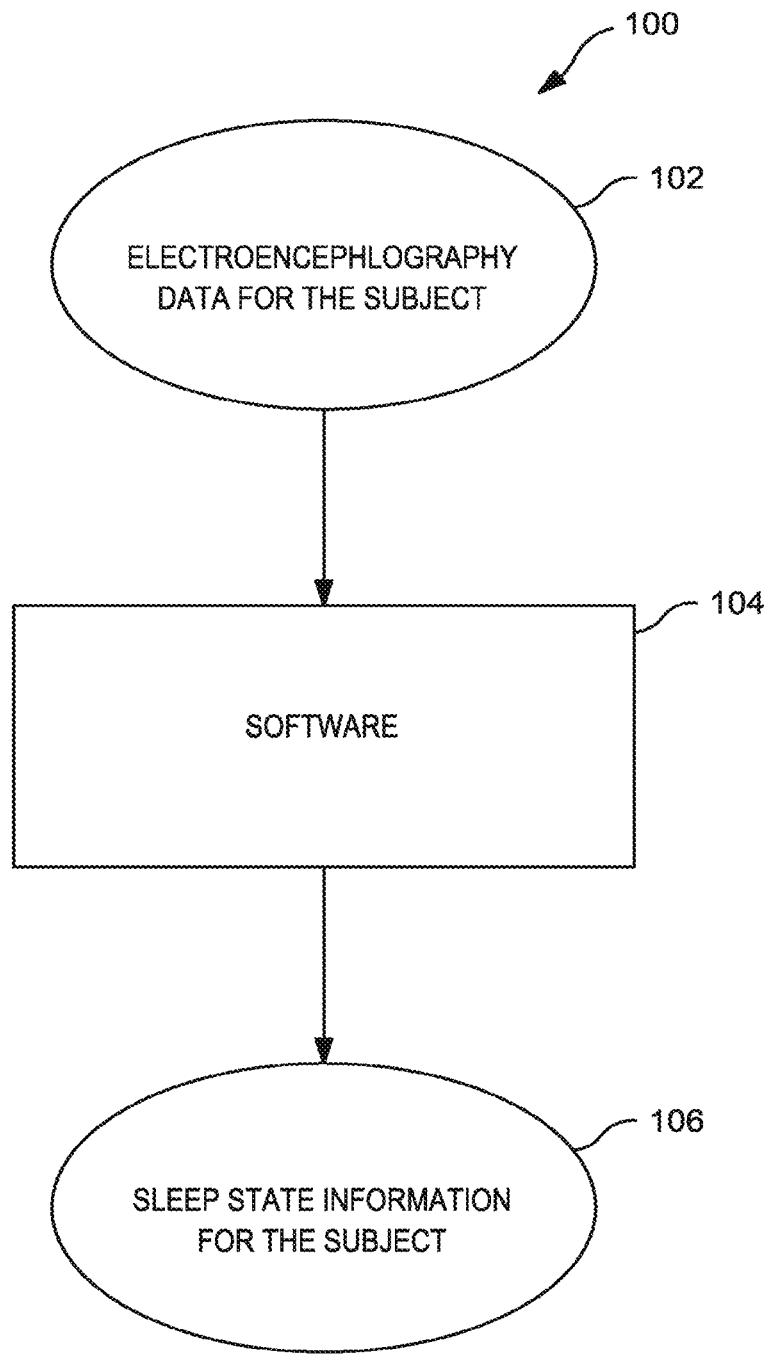
FIG. 1 is a flow diagram of an exemplary system for determining sleep state information for a subject.

Referring now to FIG. 1 which is a flow diagram of an exemplary system 100 for determining sleep state information of a subject. The EEG data 102 is received from the subject.

Exemplary Source Data

In any of the embodiments described herein, a variety of source data can be analyzed including electroencephalography (EEG) data, electrocardiography data (EKG), electrooculography data (EOG), electrocorticographic (ECoG) data, intracranial data, electromyography data (EMG), local field potential (LFP) data, magnetoencephalographic data (MEG), spike train data, wave data including sound and pressure waves, and any data exhibiting where there are differences in dynamic range of power for various frequencies across a frequency spectrum of the data e.g., a 1/f distribution. Source data can include encoded data stored at low power frequency within source data.

In one embodiment of the invention, the data 102 once received from the subject is transmitted to a software program 104 for analysis.

Exemplary System for Determining Low-Power Frequency Information from Source Data with at Least One Low Power Frequency Range Source data 102 with at least one low power frequency range is obtained and input into software 104 to determine low power frequency information.

Exemplary Method for Adjusting Source Data

Source date with at least one low power frequency range 102 is received. For example, electroencephalography source data for a subject can be received. Source data can be received via a single channel or multiple channels.

In a preferred embodiment of this invention a single channel of EEG was sufficient to decouple sleep and waking states.

Source data is adjusted to increase the dynamic range for power within at least one low power frequency range of the frequency spectrum of the source data as compared to a second higher power frequency range. A number of adjustment techniques described herein, including normalization and frequency weighting can be used.

In an embodiment, electroencephalography source data is normalized to increase the low power, higher frequency range data relative to the higher power, lower frequency range data or, more generally, to normalize the powers of the different signal parts.

After the source data is adjusted, various other processing can be done. For example, a visualization of the adjusted source data can be presented. Further, low power frequency information can be extracted from the adjusted source data. For example, low power frequency information can be extracted from adjusted electroencephalography source data. Higher power frequency information can also be extracted from the adjusted source data.

The method described in this or any of the other examples can be a computer-implemented method performed via computer-executable instructions in one or more computer-readable media. Any of the actions shown can be performed by software incorporated within a signal processing system or any other signal data analyzer system.

Referring again to FIG. 1, Electroencephalography data 102 for a subject is obtained and input into software 104 to determine sleep state information for the subject 106. The software can employ any combination of technologies, such as those described herein, to determine sleep state information for the subject.

Figure 2:
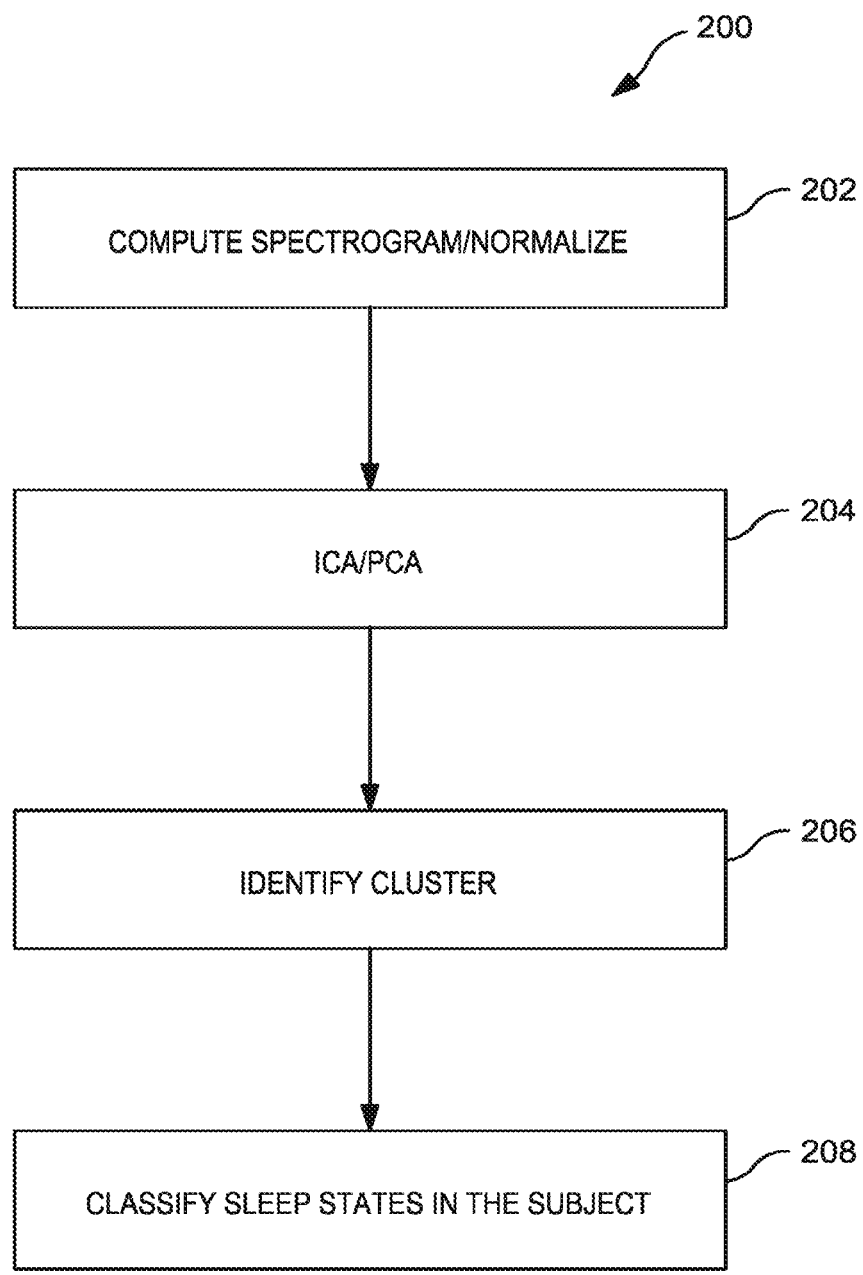
FIG. 2 is a block diagram of an exemplary system for determining sleep states for a subject.

Referring now to FIG. 2, a block diagram of an exemplary system 200 for determining sleep states of a subject wherein the data can be normalized to compute a spectrogram 202. Another embodiment uses multiple normalizations for even further dynamic range increase. Normalizations can be performed by normalizing frequency across time or time across frequency.

Exemplary Method for Adjusting Source Data to Account for Differences in Power over a Spectrum of Frequencies over Time For example, electroencephalography data with at least one low power frequency range can be received. Artifacts in the data can be removed from the source data. For example, artifact data can be manually removed from the source data or automatically filtered out of source data via a filtering (e.g., DC filtering) or data smoothing technique. The source data can also be pretreated with component analysis 204. The source data is segmented into one or more epochs; where each epoch is a portion of data from the series. For example, the source data can be segmented into a plurality of time segments via a variety of separating techniques. Scanning windows and sliding windows can be used to separate the source data into Lime series increments. The one or more epochs are normalized for differences in power of the one or more epochs across time. For example, the power of each epoch at one or more frequencies can be normalized across time to determine appropriate frequency windows for extracting information. Such normalization can reveal low power, statistically significant shifts in power at one or more frequencies (e.g., Delta, Gamma, and the like). Any frequency range can be revealed and utilized for analysis. Information can be calculated for each of the one or more epochs after appropriate frequency windows have been established. Such information can include low frequency power (e.g., Delta power), high frequency power (e.g., Gamma power), standard deviation, maximum amplitude (e.g., maximum of the absolute value of peaks) and the sort. Further calculations can be done on the information calculated for each of the one or more epochs creating information such as Gamma power/Delta power, Lime derivative of Delta, time derivative of Gamma power/Delta power and the like. Time derivatives can be computed over preceding and successive epochs. After calculating the information, that information can then be normalized across the one or more epochs. A variety of data normalization 202 techniques can be conducted including z-scoring and other similar techniques.

Results of the adjustment of source data to account for differences in power over a spectrum of frequencies over time can be presented as one or more epochs of data. For example, frequency weighted epochs can be presented as adjusted source data.

Exemplary System for Determining Sleep State Information for a Subject

Electroencephalography data for a subject is obtained and input into segmenter to segment the data into one or more epochs. In practice, epochs are of similar (e.g., the same) length. Epoch length can be adjusted via a configurable parameter. The one or more epochs, in turn, are input into normalizer 202 to normalize frequency data in the one or more epochs across time, thereby frequency weighting the one or more epochs of electroencephalography data. The one or more frequency weighted epochs are then input into classifier to classify the data into sleep states, thereby generating sleep state information for the subject 208. Methods for determining sleep state information for a subject are described in detail below.

Another Exemplary Method for Determining Sleep States in a Subject

Electroencephalography (EEG) data for a subject is received. For example, electroencephalography data, which exhibits lower dynamic range for power in at least one low power first frequency range in a frequency spectrum as compared to a second frequency range in the frequency spectrum, can be received.

The electroencephalography data for the subject is segmented into one or more epochs. For example, the EEG data can be segmented into one or more epochs via a variety of separating techniques. Scanning windows and sliding windows can be used to separate the EEG data into one or more epochs. The source data can also be filtered via direct current filtering during, prior to, or after segmenting. The source data can also be pretreated with component analysis 204 (e.g., principal or independent component analysis). In entire night EEG data the higher frequencies (e.g., Gamma) exhibit lower power than the lower frequencies (e.g., Delta, Theta and the like) in the whole night EEG data. Frequency power of the one or more epochs is weighted across time. For example, the power of each epoch at one or more frequencies can be normalized 202 across time to determine appropriate frequency windows for extracting information. Such normalization can reveal low power, statistically significant shifts in power one or more frequencies (e.g., Delta, Gamma, and the like). Additionally, each epoch can be represented by the frequency with the highest relative power over time to determine appropriate frequency windows for extracting information. Alternatively, component analysis (e.g., principal component analysis (PCA) or independent component analysis (ICA)) 204 can be utilized after normalization 202 to further determine appropriate frequency windows for extracting information. Any frequency range can be revealed and utilized for analysis.

Information can be calculated for each of the one or more epochs after appropriate frequency windows have been established (e.g., after weighting frequency). Such information can include low frequency power (e.g., Delta power), high frequency power (e.g., Gamma power), standard deviation, maximum amplitude (e.g., maximum of the absolute value of peaks) and the sort. Further calculations can be done on the information calculated for each of the one or more epochs creating information such as Gamma power/Delta power, time derivative of Delta, time derivative of Gamma power/Delta power and the like. Time derivatives can be computed over preceding and successive epochs. After calculating the information, it can then be normalized across the one or more epochs. A variety of data normalization techniques can be conducted including z-scoring and the like. The higher frequency data is now more clearly visible.

Sleep states 208 in the subject are classified based on the one or more frequency weighted epochs. For example, the one or more frequency weighted epochs can be clustered 206 by any variety of clustering techniques including k-means clustering. The clustering can be done on information calculated from the epochs (e.g., Delta power, Gamma power, standard deviation, maximum amplitude (Gamma/Delta), time derivative of Delta, time derivative-of (Gamma/Delta, and the sort). Component analysis (e.g., PCA or ICA) can be used to determine the parameter space (e.g., types of information used) in the clustering.

Subsequent to clustering 206, sleep state designations can be assigned to the epochs. Sleep state designated epochs can then be presented as representations of sleep states in the subject for the period of time represented by the epoch. Classification can also incorporate manually determined sleep states (e.g., manually determined "awake" versus "sleeping" sleep states). Additionally, artifact information (e.g. movement data, poor signal data, or the like) can be utilized in the classification.

Exemplary Sleep State Classification Techniques

Epochs can be classified according to the sleep states they represent. An epoch can be classified according to normalized variables (e.g., information calculated for an epoch) based on high frequency information, low frequency information, or both high and low frequency information. For example, REM sleep state epochs can have higher relative power than SWS at higher frequencies and lower relative power than SWS at lower frequencies. Similarly, SWS sleep state epochs can have lower relative power than REM at higher frequencies and higher relative power than REM at lower frequencies. Additionally, epochs initially classified as both NREM and NSWS sleep (e.g., epochs having low relative power at both higher and lower frequencies) can be classified as intermediate sleep and epochs classified as both REM and SWS sleep (e.g., epochs having high relative power at both higher and lower frequencies) can be classified as outliers. Further, epochs initially classified as both NREM and NSWS sleep can be classified as intermediate stage I sleep and epochs initially classified as both REM and SWS sleep can be classified as intermediate stage II sleep. Additionally, sleep states can be split in the classifying to look for spindles, k-complexes, and other parts. Any group of epochs initially classified as one sleep state can be split into multiple sub-classified sleep states according to increasing levels of classification detail. For example, a group of epochs classified as SWS can be reclassified as two distinct types of SWS Artifact data (e.g. movement data, poor signal data, and the like) can also be used in sleep state classification. For example, artifacts can be used to analyze whether epochs initially assigned a sleep state designation should be reassigned a new sleep state designation due to neighboring artifact data. For example, an epoch assigned a sleep state designation of REM that has a preceding movement artifact or awake epoch can be reassigned a sleep state designation of awake. Further, for example, an artifact epoch that has a succeeding SWS epoch can be reassigned a sleep state designation of SWS because there is a high likelihood that the epoch represents a large SWS sleep epoch rather than a large movement artifact which is more common during wakefulness. In such ways, for example, artifact data can be utilized in a data smoothing technique.

Exemplary Smoothing Techniques

Any variety of data smoothing techniques can be used during the assigning of sleep states. For example, numbers (e.g., 0 and 1) can be used to represent designated sleep states. Neighboring epochs' sleep state designation numbers can then be averaged to determine if one of the epochs is inaccurately assigned a sleep state designation. For example, abrupt jumps from SWS-NSWS-SWS (and REM-NREM-REM) are rare in sleep data. Therefore, should a group of epochs be assigned sleep state designations representing abrupt jumps in sleep states, smoothing techniques can be applied to improve the accuracy of the assigning.

Figure 3:
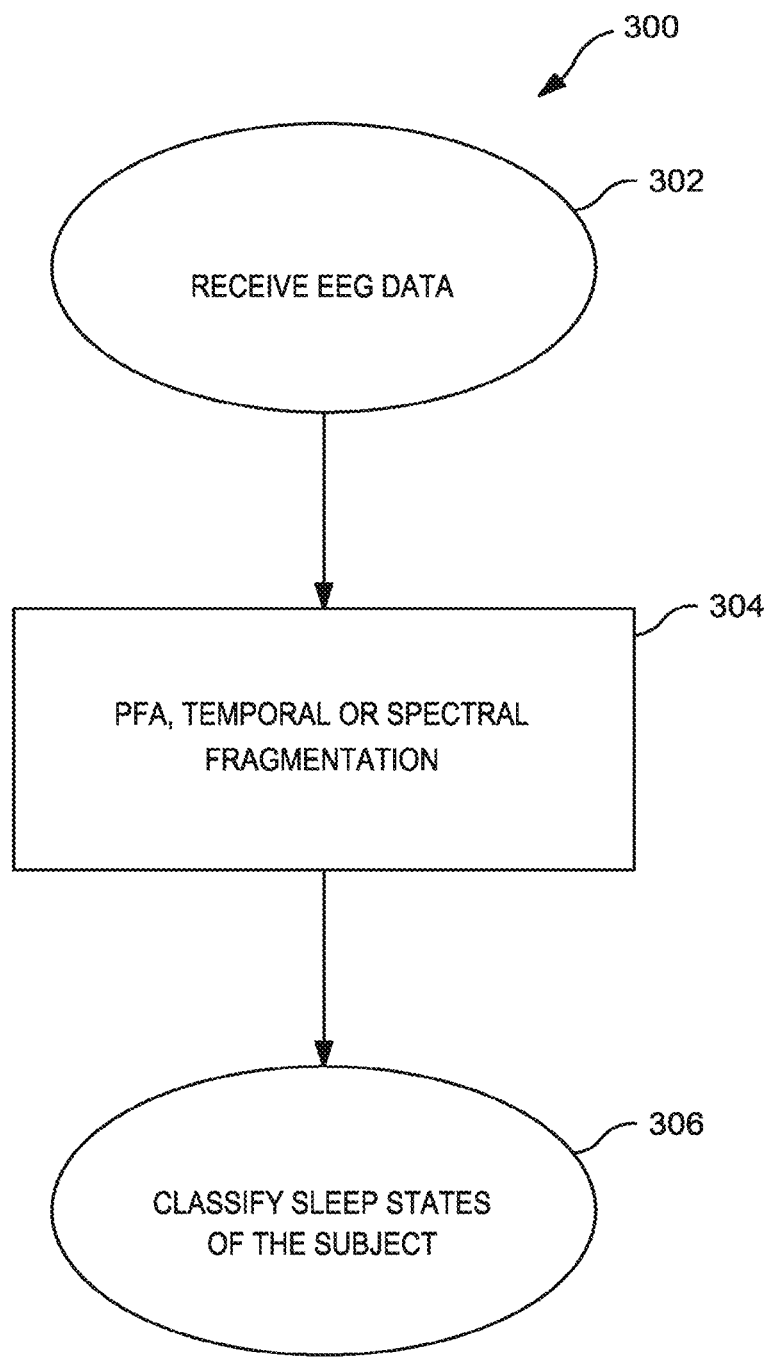
FIG. 3 is block diagram of another exemplary system for determining sleep states for a subject.

Referring now to FIG. 3, a block diagram of an exemplary system 300 for determining sleep states of a subject. The data is received from the subject 302 either manually or automatically. The Preferred Frequency Analysis, Temporal fragmentation or Spectral fragmentation 304 can be performed on the data in order to determine at least one parameter of sleep. This information can be further classified to determine a sleep state 306.

Previous embodiments have shown how normalization, for example using Z scoring, allowed analysis of more information from the brainwave signal. The analysis which was previously carried out normalized power information across frequencies. The normalization preferably used Z scoring, but any other kind of data normalization can be used. The normalization which is used is preferably unitless, like Z scoring. As well-known in the art, z scoring can be used to normalize a distribution without changing a shape of the envelope of the distribution. The z scores are essentially changed to units of standard deviation. Each z score normalized unit reflects the amount of power in the signal, relative to the average of the signal. The scores are converted into mean deviation form, by subtracting the mean from each score. The scores are then normalized relative to standard deviation. All of the z scored normalized units have standard deviations that are equal to unity.

While the above describes normalization using Z scores, it should be understood that other normalizations can also be carried out, including T scoring, and others. Multiple normalizations may also be employed. Normalizations can be performed by normalizing frequency across time or time across frequency.

The above embodiments describe normalizing the power at every frequency within a specified range. The range may be from 0, to 100 Hz, or to 128 Hz, or to 500 Hz. The range of frequencies is only restricted by the sampling rate. With an exemplary sampling rate of 30 KHz, an analysis up to 15 KHz can be done.

According to the present embodiment, additional normalizations are carried out which normalizes the power across time for each frequency. This results in information which has been normalized across frequencies and across time being used to create a normalized spectrogram. This embodiment can obtain additional information from brainwave data, and the embodiment describes automatically detecting different periods of sleep from the analyzed data. The periods of sleep that can be detected can include, but are not limited to, short wave sleep (SWS), rapid eye movement sleep (REM), intermediate sleep (IIS) and wakefulness. According to an important feature, a single channel of brainwave activity (that is obtained from a single location on the human skull) is used for the analysis. As described above, the obtained data can be one channel of EEG information from a human or other subject. The EEG data as obtained can be collected, for example, using a 256 Hz sampling rate, or can be sampled at a higher rate. The data is divided into epochs, for example 30 second epochs, and characterized according to frequency.

A first frequency normalization is carried out. The power information is normalized using a z scoring technique on each frequency bin. In the embodiment, the bins may extend from one to 100 Hz and 30 bins per hertz. The normalization occurs across time. This creates a normalized spectrogram or NS, in which each frequency band from the signal has substantially the same weight. In the embodiment, each 30 second epoch is represented by a "preferred frequency" which is the frequency with the largest z score within that epoch.

This creates a special frequency space called the Preferred Frequency space. Analysis of how those patterns are formed and analysis of the characteristics of the patterns can be done. Different sleep states, therefore, can be defined according to a discrimination function, where the discrimination function looks for certain activity in certain areas, and non-activity in other areas. The function may evaluate sleep states according to which of the frequency at areas have activity and which do not have activity.

More generally, however, any form of dynamic spectral scoring can be carried out on the compensated data. The discrimination function may require specific values, or may simply require a certain amount of activity to be present or not present, in each of a plurality of frequency ranges. The discrimination function may simply match envelopes of frequency response. The discrimination function may also look at spectral fragmentation and temporal fragmentation.

A second normalization which is carried out across frequencies. The second normalization produces a doubly normalized spectrogram. This produces a new frequency space, in which the bands become even more apparent. The doubly normalized spectrogram values can be used to form filters that maximally separate the values within the space.

A clustering technique which is carried out on the doubly normalized frequency. For example, the clustering technique may be a K means technique as described in the previous embodiments. Each cluster can represent a sleep state.

The clusters are actually multi dimensional clusters, which can themselves be graphed to find additional information. The number of dimensions can depend on the number of clustering variables. This illustrates how the doubly normalized spectrogram also allows many more measurement characteristics.

Measurement of the average spread in normalized power across frequency which illustrates the spectral fragmentation is also possible. Fragmentation values can alternatively be based on temporal fragmentation for the different states may also be used as part of the discrimination function.

These two functions are evaluated on the doubly normalized spectrum, relying on homogeneous increases in gain at all frequencies as caused movement artifacts in NREM sleep and W would lead to abnormally elevated fragmentation values in the singly normalized spectrum.

These fragmentation values may be used as part of the discrimination function. Importantly, and as described above, this discrimination function is typically not apparent from any previous analysis technique, including manual techniques.

The computation may be characterized by segmenting, or may use overlapping windows or a sliding window, to increase the temporal registration. This enables many techniques that have never been possible before. By characterizing on-the-fly, this enables distinguishing using the dynamic spectral scoring, between sleep states and awake states using the brainwave signature alone.

The exemplary methods for data analysis described above were combined with a standard non-invasive EEG method for humans. The result is the ability to non-invasively extract attenuated rhythms in animals, automatically analyze the brain activity from a single channel of EEG, and sufficiently classify the sleep parameters for the animals.

EXAMPLE 1

Rats were anesthetized with isoflurane. The scalp was gently shaved. Conductive electrogel was applied and a standard 6 mm gold plated electrode was secured with collodion. The resulting data were analyzed using advanced computational techniques, which are described above, by using software and techniques described in P.C.T. Application WO2006/1222201.

Voltage signal from the rat brain is collected by the electrodes and sent to the computer for analysis. The signal is broken down into roughly three second epochs of signal. The frequency spectra for each epoch are calculated to produce a whole recording spectrum. The resulting spectrum is then normalized across frequencies which allows for the detection of previously unidentified frequencies.

At each time epoch, only the frequency with the highest shift with respect to the baseline is mapped. The resulting map shows different signatures in this space relative to the baseline. Referring again to FIG. 2, these signatures can be used to create variables used on a multiply normalized (normalizations across time and frequency) spectrogram 202 to create a parameter space to separate stages. Component analysis 204 can also be used on the multiply normalized spectrogram to create clusters 206.

Exemplary Computational Methods for Differentiating Groups of Data

There are a wide variety of clustering and classification methods used in computational signal processing to differentiate data into distinct classes. As described herein, the clustering method used is k-means clustering but any computational signal processing method for differentiating groups of data could be used. Similarly, classification methods such as component analysis (e.g., principal and independent component analysis) are used as described herein.

An overview of computational methods is provided below.

Clustering (or cluster analysis) is unsupervised learning where the classes are unknown a priori and the goal is to discover these classes from data. For example, the identification of new tumor classes using gene expression profiles is a form of unsupervised learning.

Classification (or class prediction) is a supervised learning method where the classes are predefined and the goal is to understand the basis for the classification from a set of labeled objects and build a predictor for future unlabeled observations. For example, the classification of malignancies into known classes is a form of supervised learning.

Clustering involves several distinct steps:
Defusing a suitable distance between objects.
Selecting a applying a clustering algorithm.
Clustering procedures commonly fall into two categories: hierarchical methods and partitioning methods. Hierarchical methods can be either divisive (top-down) or agglomerative (bottom-up). Hierarchical clustering methods produce a tree or dendrogram. Hierarchical methods provide a hierarchy of clusters, from the smallest, where all objects are in one cluster, through to the largest set, where each observation is in its own cluster.

Partitioning methods usually require the specification of the number of clusters. Then, a mechanism for apportioning objects to clusters must be determined. These methods partition the data into a prespecified number k of mutually exclusive and exhaustive groups. The method iteratively reallocates the observations to clusters until some criterion is met (e.g. minimize within-cluster sumsof-squares). Examples of partitioning methods include k-means clustering, Partitioning around medoids (PAM), self organizing maps (SOM), and model-based clustering.

Most methods used in practice are agglomerative hierarchical methods, in a large part due to the availability of efficient exact algorithms. However both clustering methods have their advantages and disadvantages. Hierarchical advantages include fast computation, at least for agglomerative clustering, and disadvantages include that they are rigid and cannot be corrected later for erroneous decisions made earlier in the method. Partitioning advantages include that such methods can provide clusters that (approximately) satisfy an optimality criterion, and disadvantages include that one needs an initial k and the methods can take long computation time.

In summary, clustering is a more difficult problem than classifying for a variety of reasons including the following: there is no learning set of labeled observations the number of groups is usually unknown implicitly, one must have already selected both the relevant features and distance measures used in clustering methods.

Classifications

Techniques involving statistics, machine learning, and psychometrics can be used. Examples of classifiers include logistic regression, discriminant analysis (linear and quadratic), principal component analysis (PCA), nearest neighbor classifiers (k-nearest neighbor), classification and regression trees (CART), prediction analysis for microarrays, neural networks and multinomial log-linear models, support vector machines, aggregated classifiers (bagging, boosting, forests), and evolutionary algorithms. Logistic regression is a variation of linear regression which is used when the dependent (response) variable is a dichotomous variable (i.e., it takes only two values, which usually represent the occurrence or non-occurrence of some outcome event, usually coded as 0 or 1) and the independent (input) variables are continuous, categorical, or both. For example, in a medical study, the patient survives or dies, or a clinical sample is positive or negative for a certain viral antibody.

Unlike ordinary regression, logistic regression does not directly model a dependent variable as a linear combination of dependent variables, nor does it assume that the dependent variable is normally distributed. Logistic regression instead models a function of the probability of event occurrence as a linear combination of the explanatory variables. For logistic regression, the function relating the probabilities to the explanatory variables in this way is the logistic function, which has a sigmoid or S shape when plotted against the values of the linear combination of the explanatory variables.

Logistic regression is used in classification by fitting the logistic regression model to data and classifying the various explanatory variable patterns based on their fitted probabilities. Classifications of subsequent data are then based on their covariate patterns and estimated probability Discriminant analysis:

In summary discriminant analysis represents samples as points in space and then classifies the points. Linear discriminant analysis (LDA) finds an optimal plane surface that best separates points that belong to two classes. Quadratic discriminant analysis (QDA) finds an optimal curved (quadratic) surface instead. Both methods seek to minimize some form of classification error.

Fisher linear discriminant analysis (FLDA or LDA):

LDA finds linear combinations (discriminant variables) of data with large ratios of between-groups to within-groups sums of squares and predicts the class of an observation x by the class whose mean vector is closest to x in terms of the discriminant variables. Advantages of LDA include that it is simple and intuitive where the predicted class of a test case is the class with the closest mean and it is easy to implement with a good performance in practice.

Nearest neighbor classifiers:

Nearest neighbor methods are based on a measure of distance between observations, such as the Euclidean distance or one minus the correlation between two data sets. K-nearest neighbor classifiers work by classifying an observation x as follows;

find the k observations in the learning set that are closest to x.

predict the class of x by majority vote, i.e., choose the class that is most common among these k neighbors. Simple classifiers with k=1 can generally be quite successful. A large number of irrelevant or noise variables with little or no relevance can substantially degrade the performance of a nearest neighbor classifier.

Figure 4:
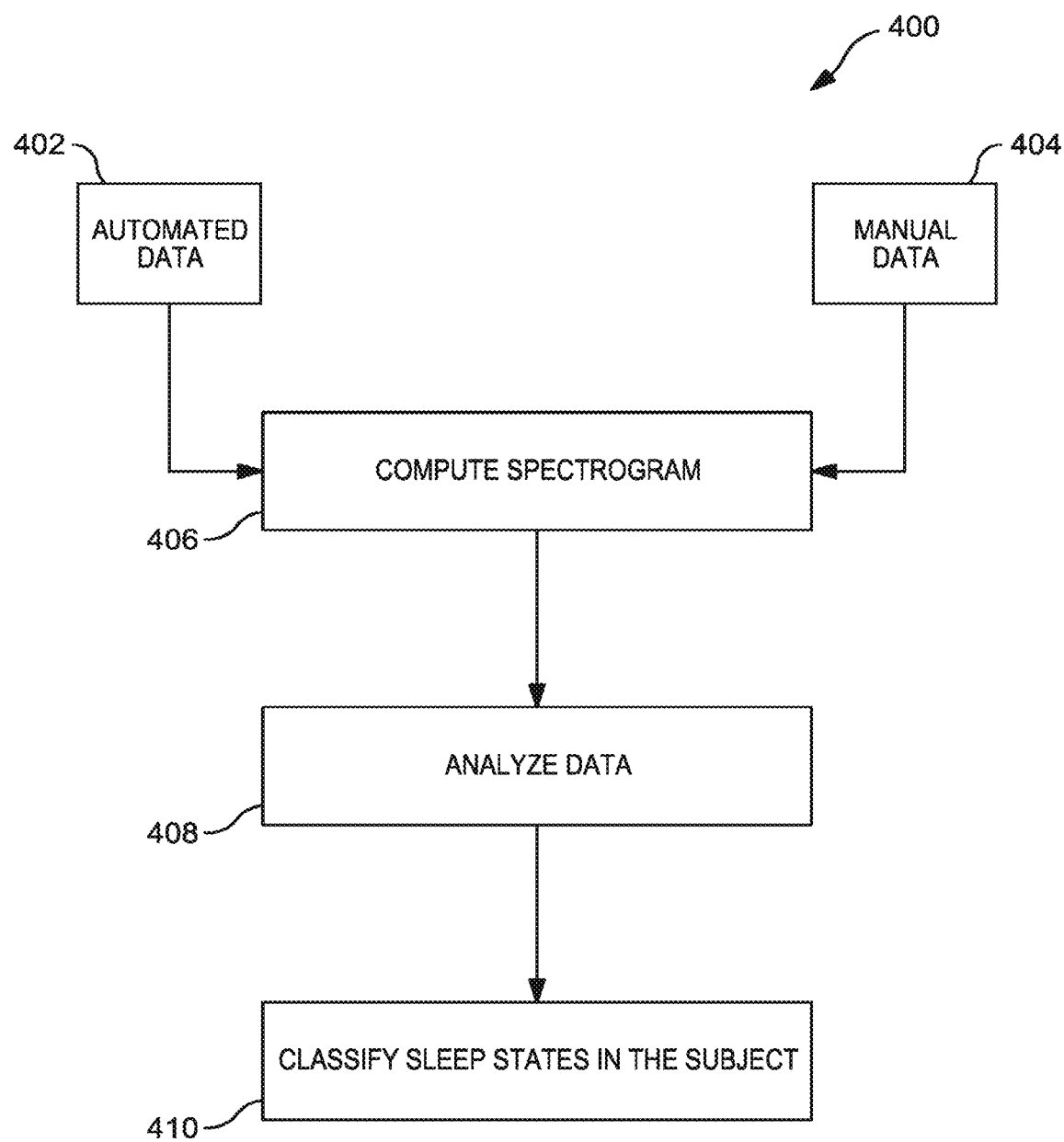
FIG. 4 is a block diagram of an exemplary system for determining sleep states for a subject utilizing either automated data or manual data.

Referring now to FIG. 4, an exemplary system for determining sleep states for a subject utilizing either automated data or manual data 400. Automated data 402 as well as manually scored data 404 can be used to compute the spectrogram 406. The methods described above can be applied to analyze the data 408 and subsequently determine sleep state information for the subject 410

Example 2 illustrates how the exemplary methods can be applied to determine sleep patterns from a single channel of EEG using either automated or manual data.

EXAMPLE 2

One channel of EEG (C3-A2 derivation) from twenty-six nights (8 hours each) of sleep was obtained from twenty-six different polysomnographic recordings conducted in twenty-six healthy human subjects. The EEG data and manual scoring was provided by the experimental procedures were approved by the Institutional Review Boards at each institution.

EEG data were collected at 256 Hz and bandpassed at 0.3-100 Hz with a 60 Hz notch filter (UCSD) or collected at 250 Hz and bandpassed at 0.53-70 Hz (MPI). These recordings were amplified at 10 K and manually scored in 30 sec epochs in accordance with R-K. For each recording, the whole night spectrogram was computed over 2 orthogonal tapers on 30 sec epochs using a standard multitaper technique. The power information was then normalized by z-scoring for each frequency bin (from 1 to 100 Hz, 30 bins per Hz) across time. This normalized spectrogram (NS) weighed each frequency band equally. Each 30 second segment was represented by the frequency with the largest z-score. In this preferred frequency space (PFS), sleep and waking states broadly separated into different patterns (FIGS. 21, 22.) W was always characterized by a band in alpha (7-12 Hz) and sometimes by a band in beta (15-25 Hz). IS exhibited prominent activity in the spindle frequencies (12-15 Hz). Surprisingly, REM was defined by compact bands in theta (4-8 Hz) and sometimes beta (15-25 Hz) frequencies whereas SWS was dominated by delta activity. When computed over overlapping 3 sec windows and a 1 sec sliding window, similar trends were visible in the PFS except that beta activity emerged in REM. At that resolution, REM appears more "awake-like" than at a 30 sec resolution. However, at that resolution, all the sleep states whether they were identified manually or automatically had distinct signatures in the Preferred Frequency Space.

At each time point, z-scoring the Normalized Spectrogram across frequencies creates a doubly normalized spectrogram. In this space, bands apparent in the PFS still had positive values whereas dark regions tended to have negative values. By adding the double normalized spectrogram values of frequencies that show up as bands in the PFS and subtracting those that do not, filters can be constructed that maximally separate states. One maximizes W ('W filter"), another separates NREM from W and REM ('NREM filter') and a third distinguishes IS from SWS ('SWS filter'). The output of these three filters spans a space in which the three broad sleep stages and W tend to separate.

Interestingly, Stage I did not cluster in either space and SWS formed only one cluster (rather than two, one for Stage III and one for Stage IV). The latter is in accordance with the recent revision of R-K which abandoned the Stage III/IV distinction. Manual scoring of Stages I and III was done in 30 sec increments. At that resolution, epochs manually labeled as Stage III could not be disambiguated from epochs manually labeled as Stage II or Stage IV in the majority of recordings and epochs manually labeled as Stage 1 could not be distinguished from epochs manually labeled as Stage II, REM or W in most recordings in the PFS. Thus it is conceivable that Stages I and III are not stationary sleep states per se but rather are transitional. However REM was easily distinguishable from Waking. Thus, human REM sleep should no longer be thought of as "awake-like" or "paradoxical".

A K-means clustering algorithm (FIG. 20) was applied to the normalized data in the spaces above to classify sleep states. Even though the VA and MPI data were filtered differently, the general position of the sleep and waking clusters was similar across sets. Moreover, although the algorithm was optimized on the MPI data set, it performed at 80.6% on the VA data, which is unprecedented using a single channel of data and is similar to the performance of other algorithms using many more channels. (Flexer, A., et al., *Artif Intell Med.* 33, 199 (2005). The standard error of the mean was also lower for the VA set than the MPI set even though the former had 6 subjects and the latter had 20 subjects (1.73% vs. 1.78%, respectively). The average agreement rate with human scoring on the full data set was 77.58% on 4 stages. This striking concordance can be visualized by overlapping automated and manually derived hypnograms, which plot sleep stages for a given subject over a given night. In two out of twenty-six recordings, it appeared that the algorithm was mislabeling the data and in these cases. While that data appeared different when compared to the rest of the data set, visualization of the manual scoring on the preferred frequency map did however show separate signatures for sleep and waking stages. On the VA data, when the algorithm's performance was compared against data rescored by the same person or scored by a more experienced scorer, the average agreement rate with the algorithm increased and was in the 82.4-83.3% range.

Figure 7:
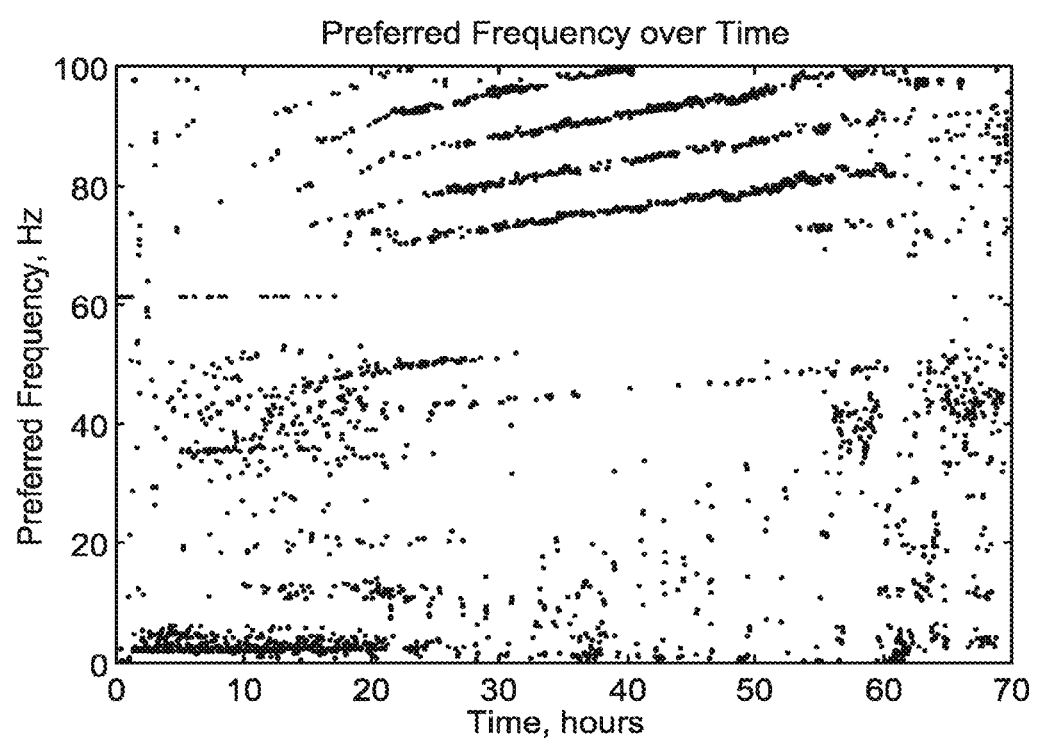
FIG. 7 is the result of Preferred Frequency analysis. Each dot corresponds to the frequency with the highest shift with respect to baseline, independently.
Figure 8:
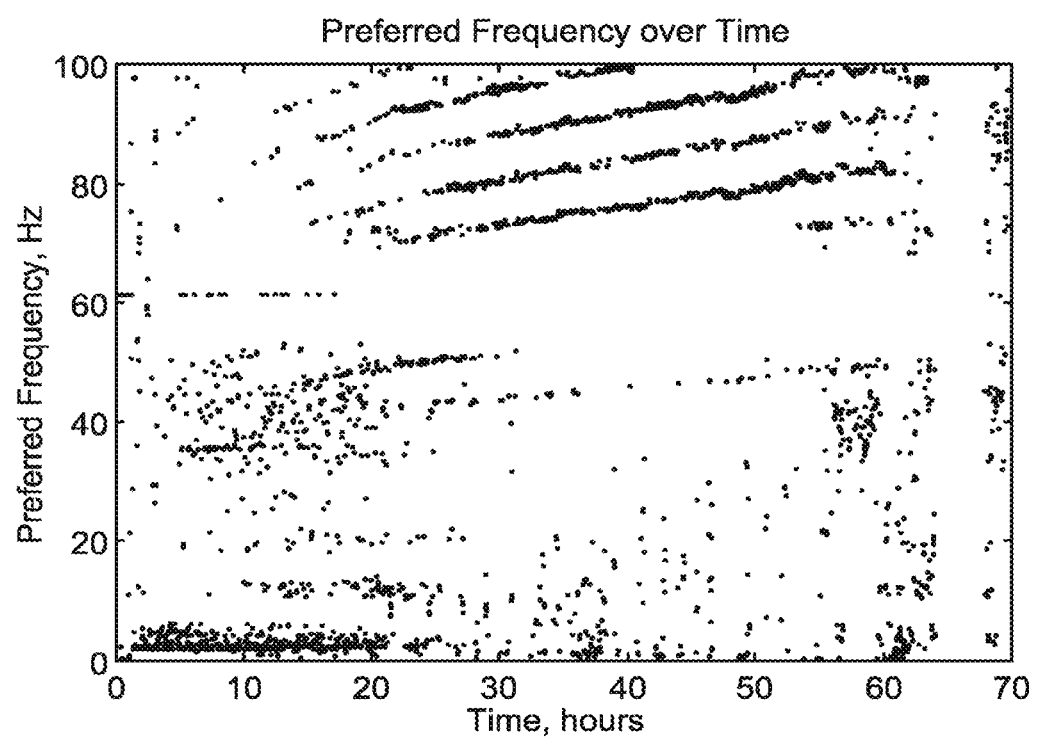
FIG. 8 is the result of coloring the Preferred Frequency analysis plot of FIG. 1*b* to reflect stages of behavior scored in a blind manner, independently of EEG. Dots correspond to 1 second.
Figure 9:
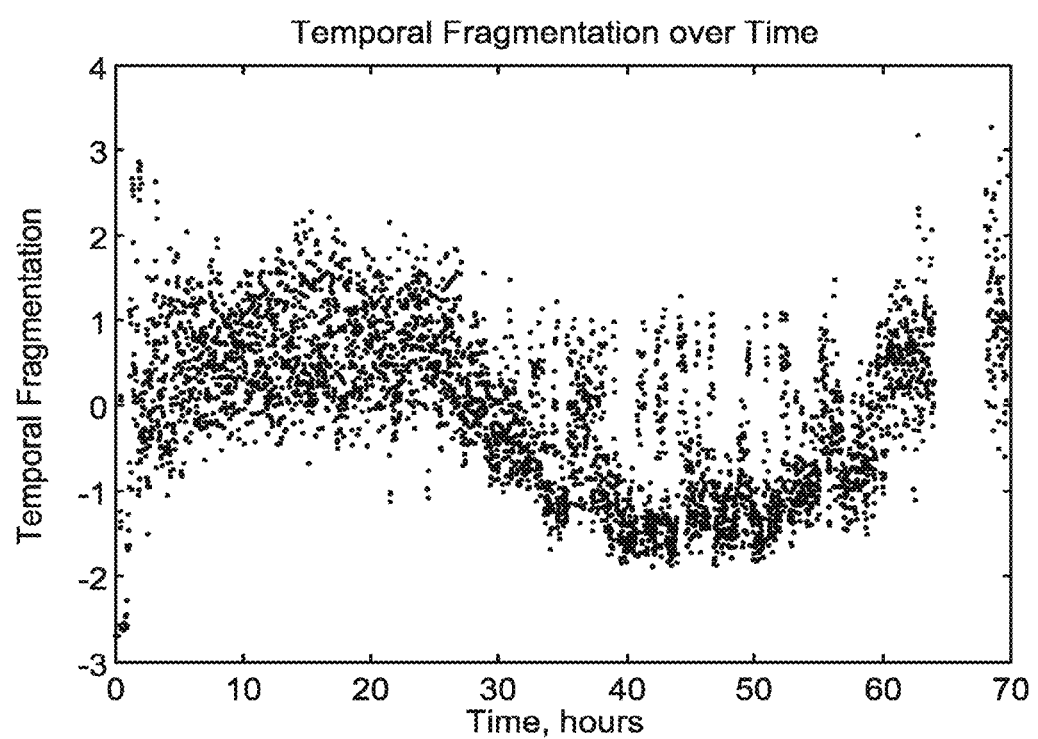
FIG. 9 is the result of Temporal Fragmentation corresponding to the sparseness of spectral shifts in time which demonstrate the sensitivity of the Preferred Frequency plots to peak fluctuations in normalized power.
Figure 10:
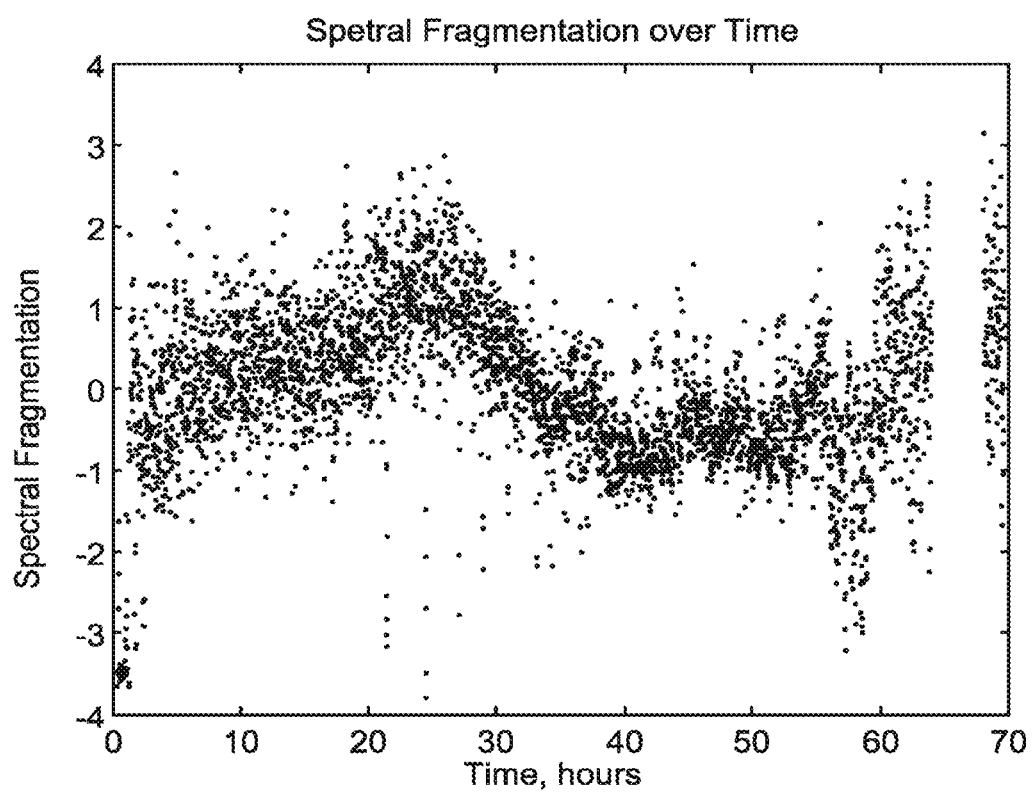
FIG. 10 is the result of Spectral Fragmentation corresponding to the sparseness of spectral shifts within the spectrum at a given time which demonstrate the sensitivity of the Preferred Frequency plots to peak fluctuations in normalized power.
Figure 11:
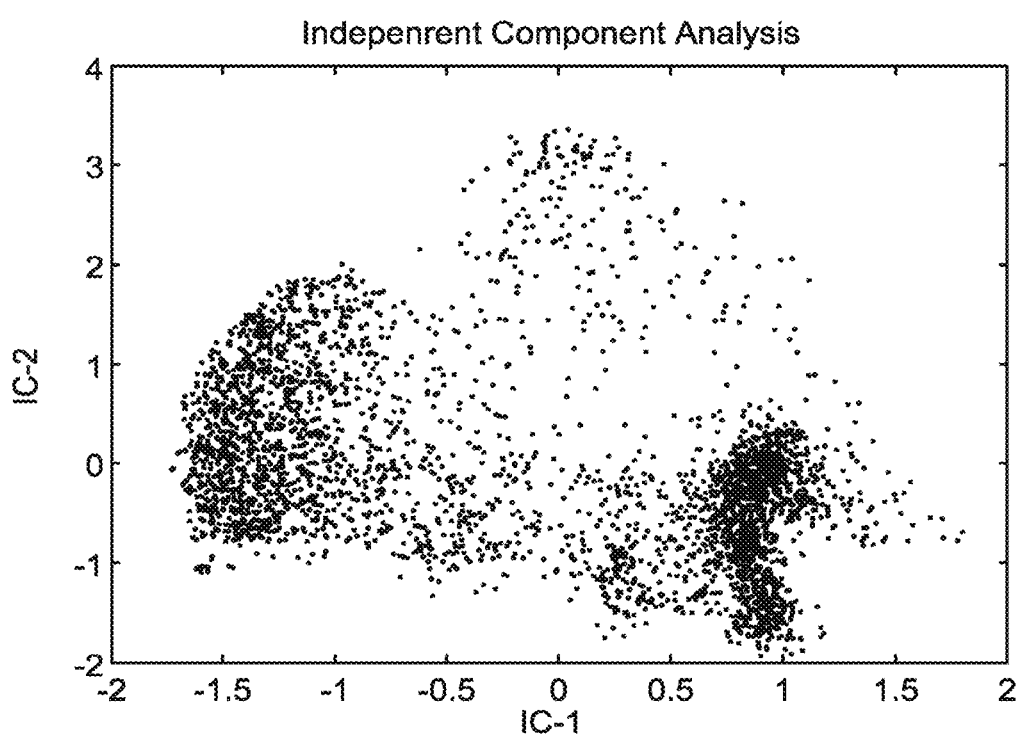
FIG. 11 is the result of using Independent Component Analysis on a single channel, as part of SPEARS to demonstrate the emergence of three clusters: deep anesthesia (blue), waking (yellow and red), and twitches (magenta).
Figure 12:
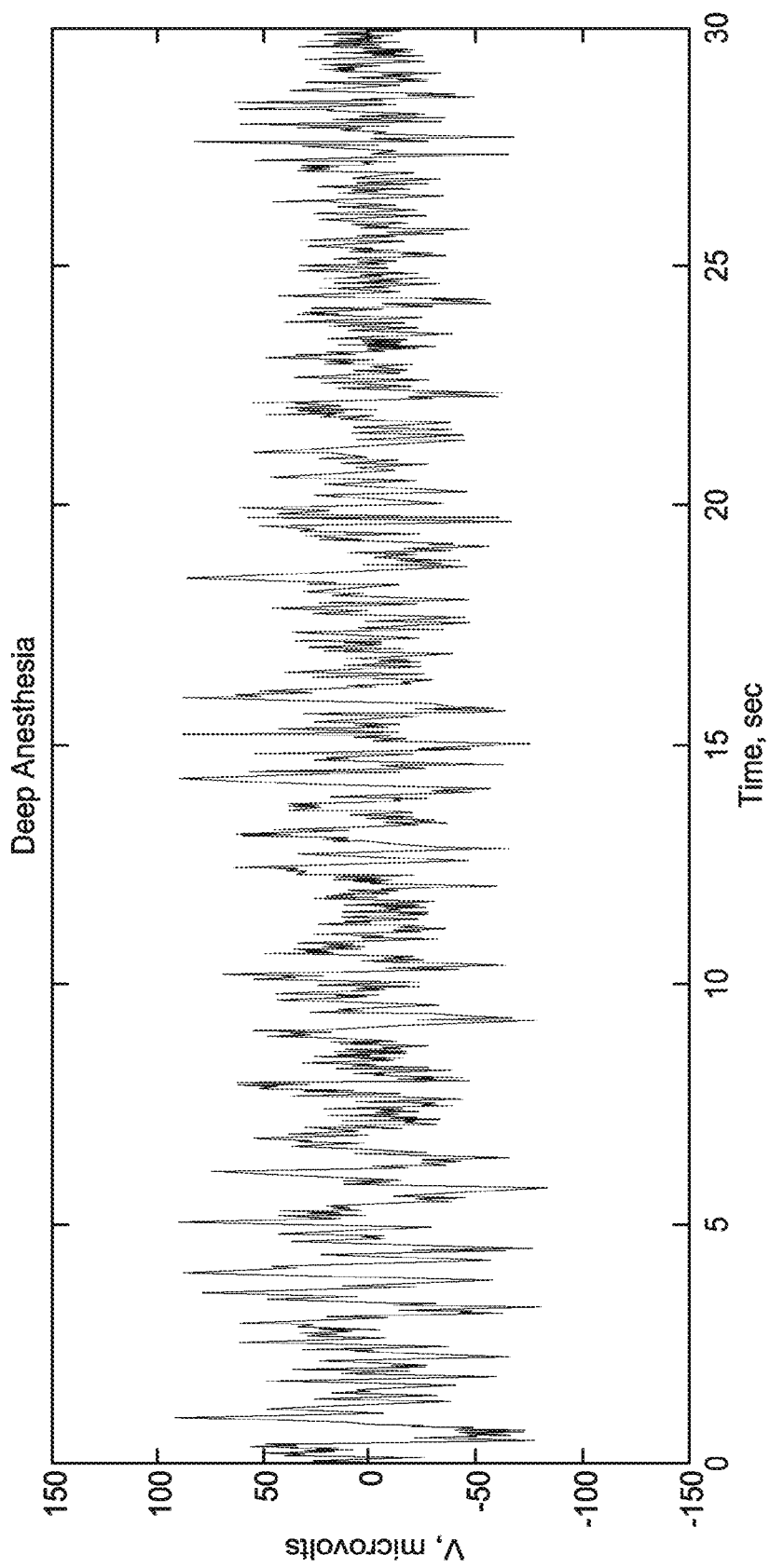
FIG. 12 is the result of displaying 30 seconds of raw EEG data for deep anesthesia.
Figure 13:
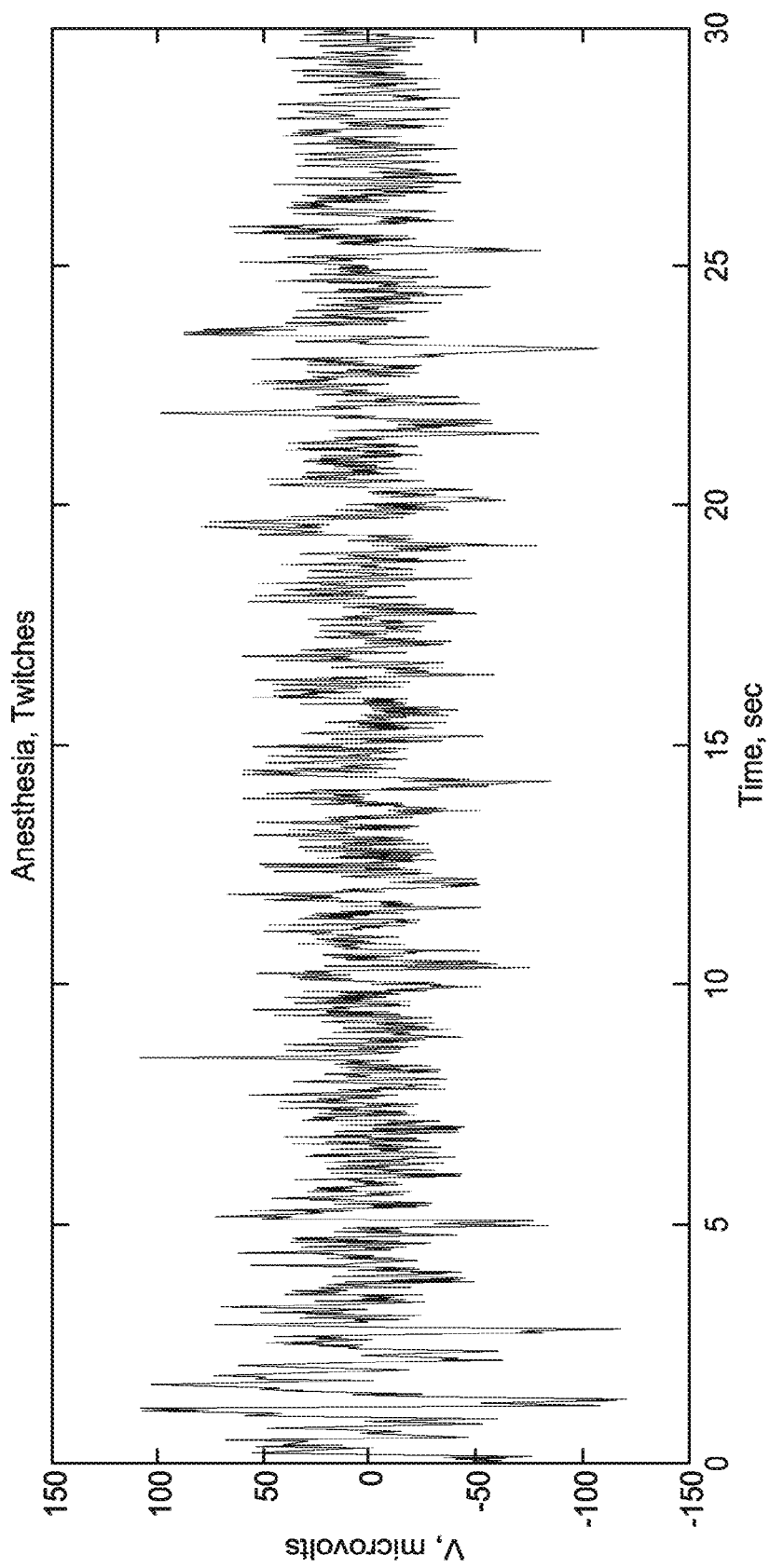
FIG. 13 is the result of displaying 30 seconds of raw EEG data for lighter anesthesia with twitches.
Figure 14:
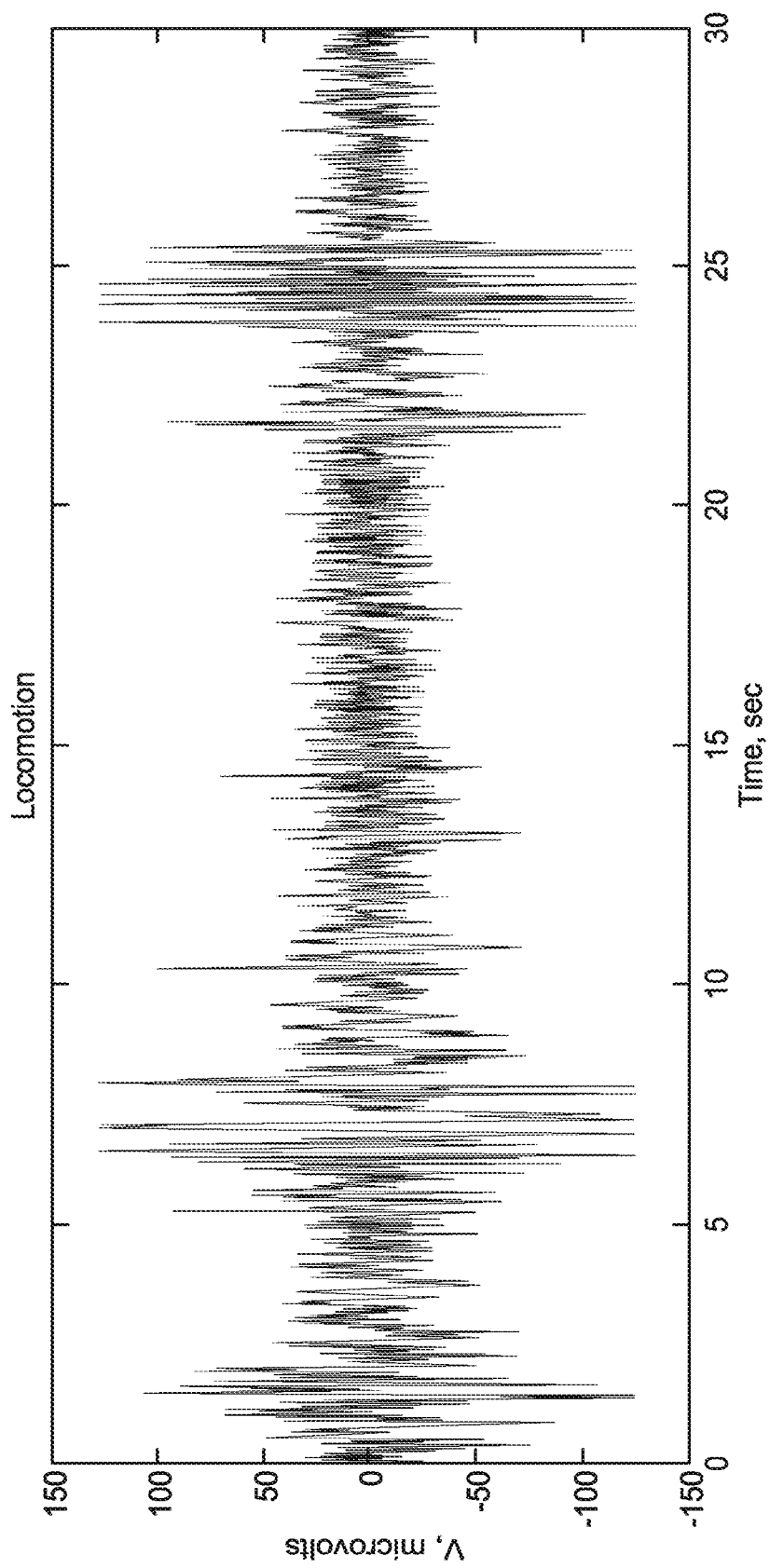
FIG. 14 is the result of displaying 30 seconds of raw EEG data for locomotion.
Figure 15:
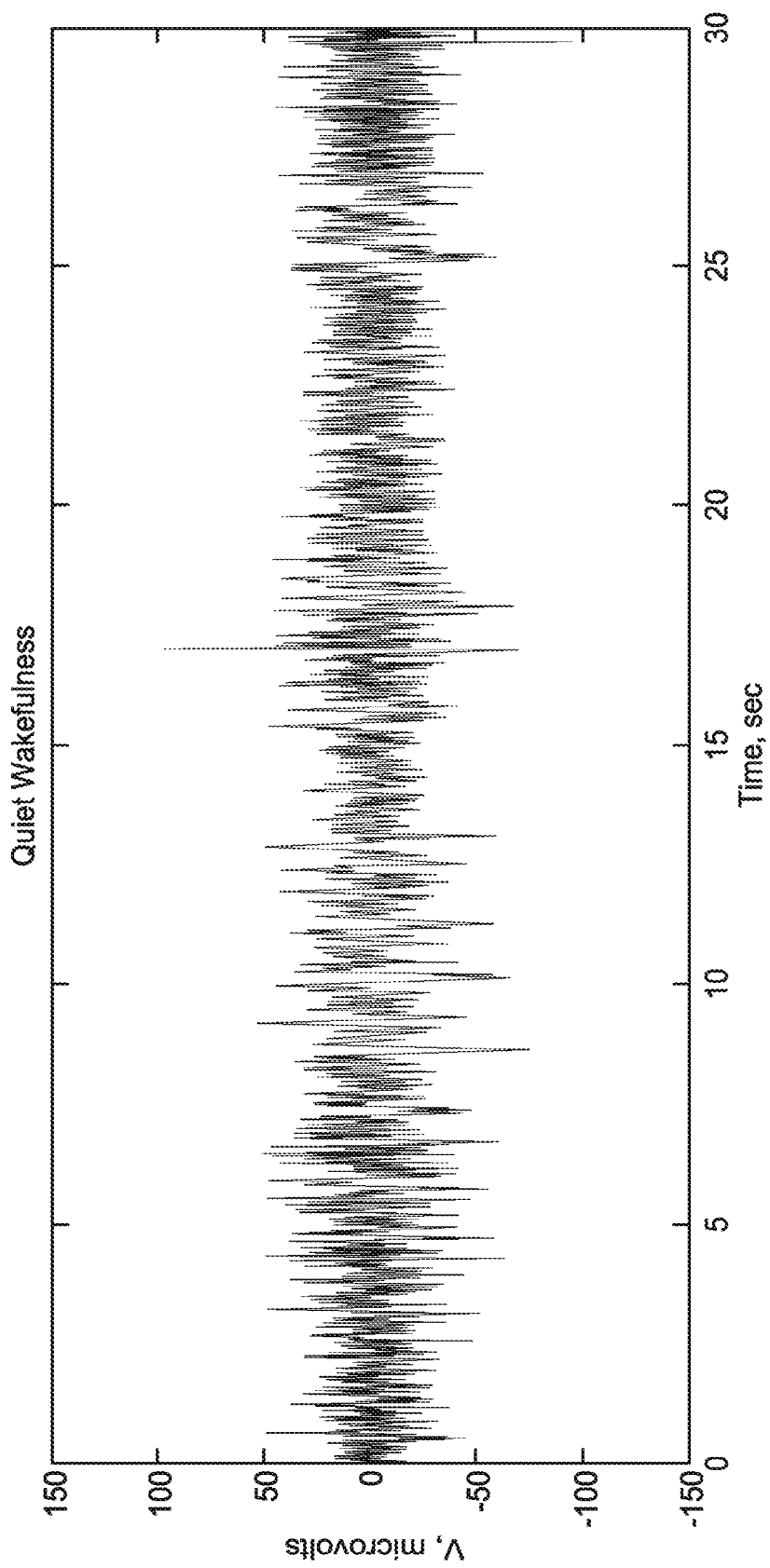
FIG. 15 is the result of displaying 30 seconds of raw EEG data with movement artifacts and quiet wakefulness.

Further normalizations in time and frequency can be applied to the whole night spectrogram, at both a 30 sec (FIG. 7 a,c, FIG. 8) and a 1 sec resolution (FIG. 7b,d, FIG. 9). Here sleep and waking stages tile the entire 1-100 Hz spectrum with REM, W and IS exhibiting broadband patterns (FIG. 8, FIG. 9c-d).

Figure 16:
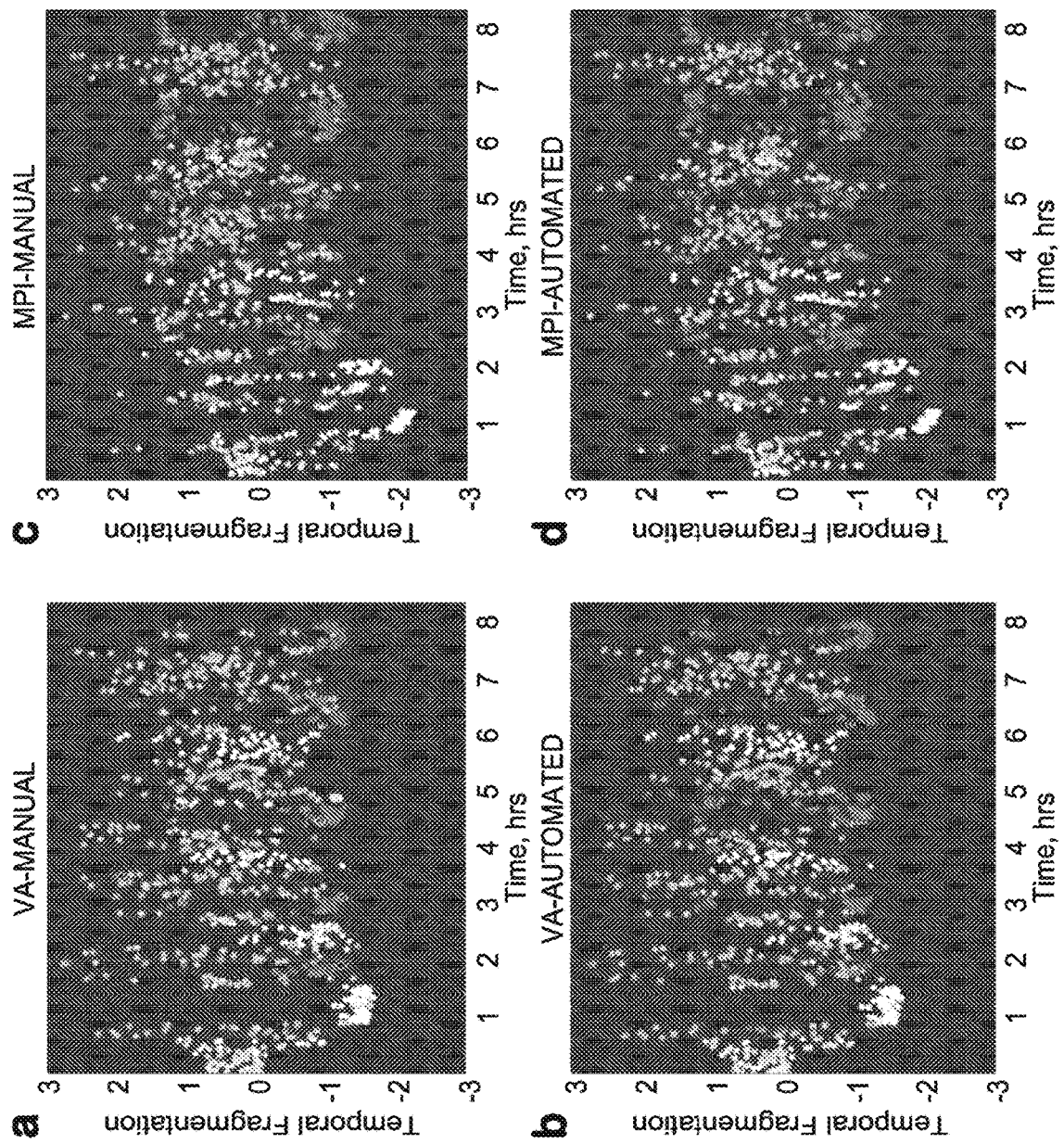
FIG. 16 is the Bimodal Temporal Fragmentation of REM sleep. The temporal fragmentation was computed at a 30 second resolution for two different sleep recordings of two different subjects (a-b, c-d). Labels are drawn from either manual (a, c) or automated (b, d) scoring. REM sleep, in red, split into two different groups with either high or low temporal fragmentation. This was apparent in both recordings, independently of whether manual or automated algorithm performed the scoring.

In this space, one can measure the fragmentation in normalized power across time (temporal fragmentation) (FIGS. 16, 21-22). This analysis revealed a bimodal distribution for REM sleep. This pattern persisted when the frequency range was narrowed to 4-40 HZ (data not shown). The more fragmented part of REM accounted for (mean±s.e.m) 26.18±1.7% of REM at a rate of 37.42±2.70 epochs per night lasting an average of 36.18±1.27 seconds and separated by an average of 129.08±11.04 seconds of stable REM (FIG. 28). These components of REM do not correspond to tonic and phasic REM (FIG. 29) and exhibit different spectral signatures (FIG. 23). This unstable part of REM sleep was more likely to be confused with stage II than the stable part (FIGS. 31-32). In these cases some spindles and K-complexes in the presence of REM caused these epochs to be scored as stage II (FIG. 21) even though they would have been scored as REM at a finer temporal resolution. According to R-K rules, no spindles or K-complexes can be separated by less than 3 minutes in REM. While K-complexes and spindles can be found in REM, according to the analysis presented here, these signals are not responsible for the bimodal temporal fragmentation pattern observed in REM since manually scored REM, presumably devoid of spindles and K-complexes, still exhibits this pattern (FIG. 16 a-b, 21-22, 31 right columns). Moreover, REM still exhibited a bimodal distribution on a spectrum without spindle frequency power. The temporal fragmentation is sensitive to sudden changes in normalized power. Such changes can also be brought about by artifacts and the changes they produce will be enhanced in the background of a low power EEG. Therefore, artifacts of some sort could be responsible for most if not all of the bimodal temporal fragmentation of REM. When epochs adjacent to epochs known to contain movement artifacts were discarded from the analysis as well as any epoch having a preferred frequency greater than 25 Hz, the percentage of unstable REM epochs was diminished even if the bimodal pattern could still be seen. The bimodal pattern was even less apparent when more artifacts were isolated. However when these artifacts were included in the fragmentation analysis, in 4 out of 6 cases (5 out of 6 cases when REM was visually identified by a second scorer), they accounted for a higher percentage of the non-fragmented portion of REM (6 out of 6 for automated scoring) and in all but two cases for manual scoring (non-fragmented portion of REM_71.91% in subject 9 and 50.73% and 52.24% in subject 20, depending on the scorer) and in all but one case for automated scoring (non-fragmented portion of REM 75.9% in subject 9), they accounted for less than 50% of either portion of REM. A nearest-neighbor analysis was performed on epochs which did not themselves include artifacts (FIG. 33). The fragmented portion of REM had almost in all cases more neighbors which contained an artifact than the non-fragmented portion, according to manual scoring (5/6 subjects for one scorer 6/6 subjects for the other). When REM was detected automatically, in most subjects, the majority of both the fragmented and non-fragmented epochs were devoid of neighboring artifacts. Further analysis of these data will be necessary to identify EEG features that might be responsible for the observed patterns and possibly a new state of sleep. Nevertheless, temporal fragmentation provides yet another variable that easily distinguishes REM from both W and Stage I (FIG. 30).

Exemplary Sleep Statistics

In any of the technologies described herein, any variety of statistics can be generated from adjusted source data. For example, sleep statistics can be generated from adjusted source EEG data that has been classified into sleep states. Exemplary sleep statistics can include information including sleep stage densities, number of sleep stage episodes, sleep stage average duration, cycle time, interval time between sleep stages, sleep stage separation statistics, onset of sleep, rapid eye movement sleep latency, regression coefficients of trends, measures of statistical significance of trends, and the like.

Exemplary Sleep Data Presenter

In any of the examples herein, an electronic or paper-based report based on sleep state data can be presented. Such reports can include customized sleep state information, sleep state statistics, pathological conditions, medication and/or chemical effects on sleep, and the like for a subject. Recommendations for screening tests, behavioral changes, and the like can also be presented. Although particular sleep data and low frequency information results are shown in some examples, other sleep data presenters and visualizations of data can be used.

Exemplary Computer Implemented Methods

Any of the computer-implemented methods described herein can be performed by software executed by software in an automated system (for example, a computer system). Fully-automatic (for example, without human intervention) or semiautomatic operation (for example, computer processing assisted by human intervention) can be supported. User intervention may be desired in some cases, such as to adjust parameters or consider results.

Such software can be stored on one or more computer-readable media comprising computer-executable instructions for performing the described actions. Such media can be tangible (e.g., physical) media.

The above has described how information can be used to determine sleep states. These techniques may also be used for other applications including characterizing sleep states, and other techniques. Applications may include determination of whether a patient has taken certain kinds of drugs based on their sleep state, and based on variables that were previously determined as changing in brain function based on those sleep states.

Figure 5:
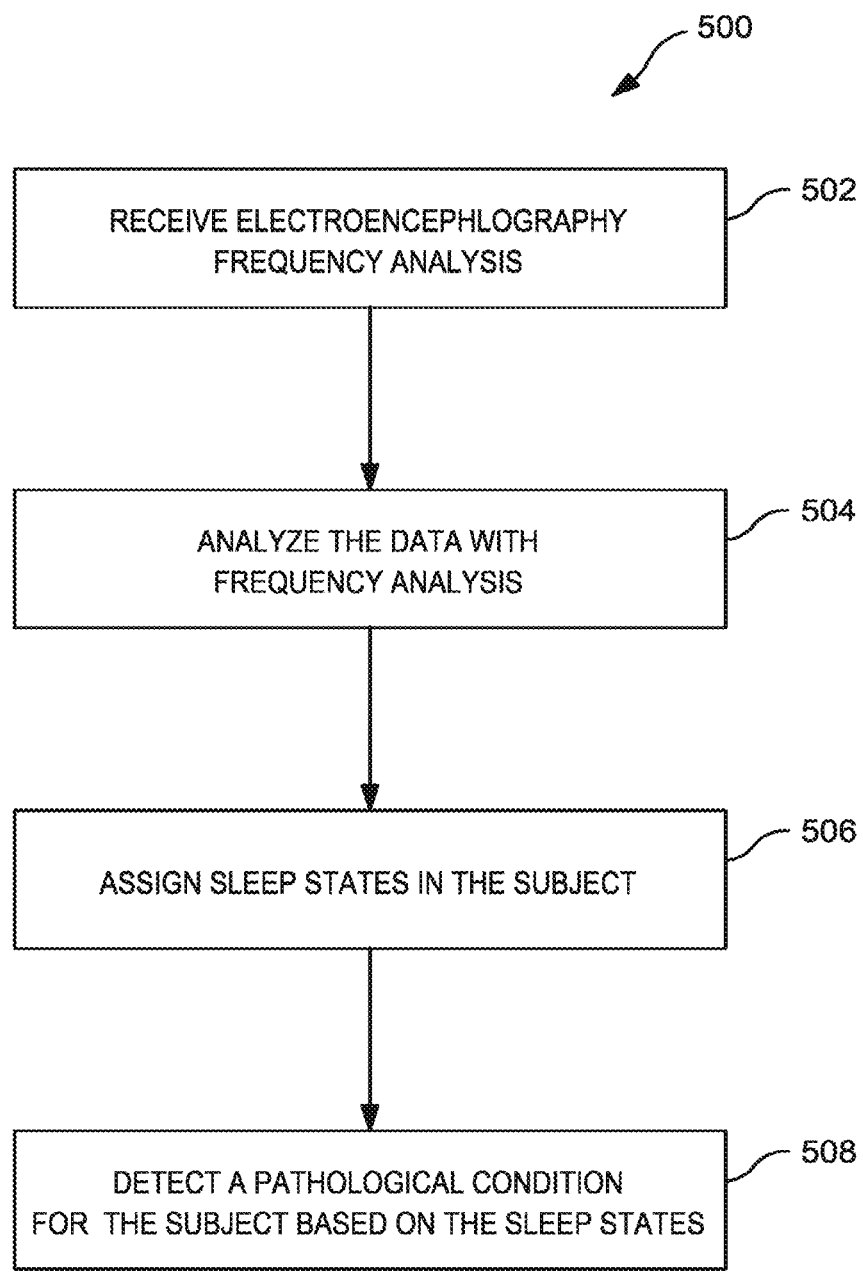
FIG. 5 is a block diagram of an exemplary system for determining a pathological condition of a subject from sleep states.
Figure 6:
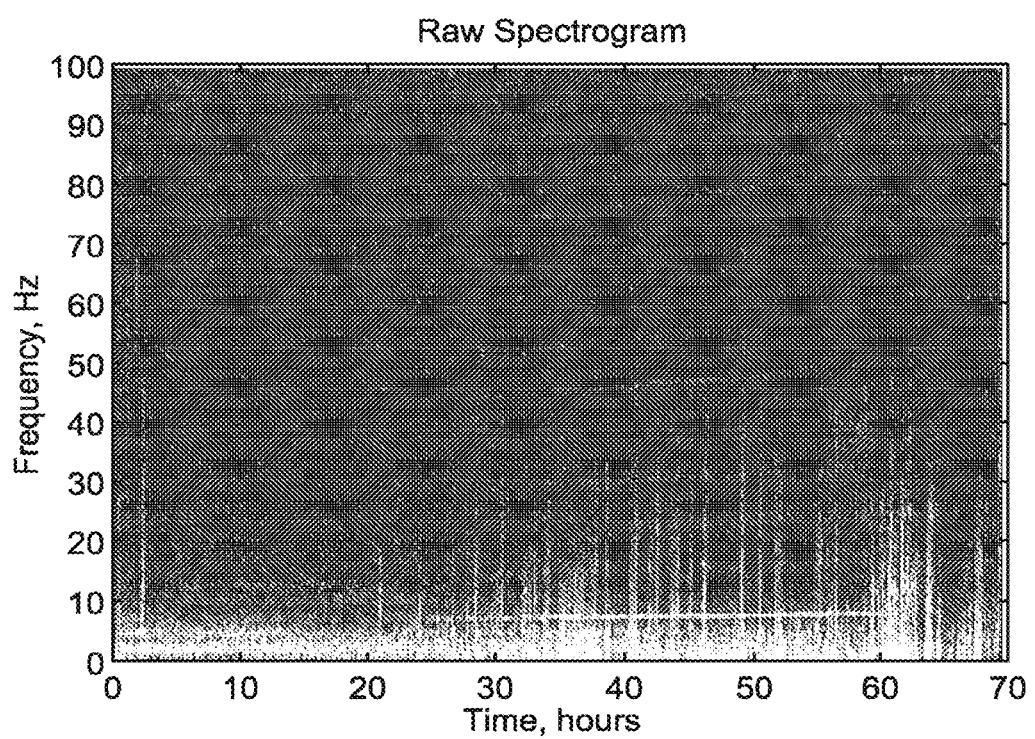
FIG. 6 is the result of one channel of a rat EEG converted into a spectrogram with a multitaper analysis using a 3 second spectral window, and a 1 second sliding window. The light gradient is indicative of the spectral power at each frequency with light reflecting high power and black, low power. Dots correspond to 1 second.

Referring now to FIG. 5, which is a block diagram showing an Exemplary System for Determining a Pathological Condition of a Subject from Sleep States 500. Electroencephalography data for an animal is obtained and input into sleep state analyzer to determine a pathological condition of the subject.

A pathological condition can be detected in an animal based on the sleep states 506. For example, sleep states can be acquired for an animal 502 and analyzed 504 to determine whether the sleep states represent normal sleep or abnormal sleep. Abnormal sleep could indicate a pathological condition 508. For example, sleep states can be acquired from animals with pathological conditions and analyzed for common attributes to generate an exemplary distinctive "pathological condition" sleep state profile and/or sleep state statistics representative of having the pathological condition. Such a profile or statistics can be compared to sleep states determined for an animal in order to detect whether the subject has the pathological condition or any early indicators of the pathological condition. Any variety of pathological conditions can be detected and/or analyzed. For example, sleep related pathological conditions can include epilepsy, Alzheimer's disease, depression, brain trauma, insomnia, restless leg syndrome, and sleep apnea. For example, polysomnographically, subjects with Alzheimer's can show decreased rapid eye movement sleep in proportion to the extent of their dementia.

Narcolepsy is associated with sudden transitions into REM. It has recently been reported that there are instability patterns in the EEG of narcoleptic animals. If these apply to REM and humans as well, narcoleptics may have a marked difference in their REM fragmentation patterns as well.

Many other diseases have been linked to sleep disorders. For example, depression is associated with short REM latency and increased REM sleep. Parkinson's disease is also associated with REM behavior disorder. Alzheimer's patients already have unstable sleep patterns. These conditions and their treatment (MAOIs, used against depression block REM; cholinesterase inhibitors, used against Alzheimer's disease, affect REM as well) may be associated with new expressions of stable and unstable REM, which could be used to assess both pathology and treatment.

The preferred frequency and iterated preferred frequency plots could also help to extract biomarkers of pathology and treatment.

Exemplary Medications and Chemicals that can Affect Sleep

In any of the technologies described herein, the effect of medications and chemicals on sleep states of an animal can be determined via analyzing source data obtained for an animal. For example, sleep states can be modified by alcohol, nicotine, and cocaine use. Exemplary medications that affect sleep include steroids, theophylline, decongestants, benzodiazepines, antidepressants, monoamine oxidase inhibitors (e.g., Phenelzine and Moclobemide), selective scrotonin reuptake inhibitors (e.g., Fluoxetine (distributed under the Prozac® name) and Sertralie (distributed under the Zoloft® name), thyroxine, oral contraceptive pills, antihypertensives, antihistamines, neuroleptics, amphetamines, barbiturates, anesthetics, and the like.

Sleep patterns may be used as a diagnostic as described above for pathological conditions and medication effects. The example below illustrates how sleep patterns may be used as a biomarker to identify individuals.

EXAMPLE 3

Sleep data for four pairs of twins were analyzed utilizing the exemplary sleep staging techniques described above.

Each column in 1-4 corresponds to 4 pairs of twins (pair 1 is fraternal, pairs 2-4 is identical). Only REM is shown (temporal fragmentation across time). Twins exhibit a similar temporal fragmentation pattern (FIG. 34).

EXAMPLE 4

FIG. 35 depicts two Preferred Frequency plots, before and after administration of a drug to a subject. The plots evidence detection via the methods described herein of the disappearance of Stage II sleep spindles after the administration of drug.

The general structure and techniques, and more specific embodiments which can be used to effect different ways of carrying out the more general goals are described herein.

Throughout this application, various publications, patents, and/or patent applications are referenced in order to more fully describe the state of the art to which this invention pertains. The disclosures of these publications, patents, and/or patent applications are herein incorporated by reference in their entireties, and for the subject matter for which they are specifically referenced in the same or a prior sentence, to the same extent as if each independent publication, patent, and/or patent application was specifically and individually indicated to be incorporated by reference.

Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, other applications are possible, and other forms of discrimination functions and characterization is possible. While the above extensively described characterizing the frequency in terms of its "preferred frequency", it should be understood that more rigorous characterization of the information may be possible. Also, while the above only refers to determining sleep states from the EEG data, and refers to only a few different kinds of determination of sleep states, it should be understood that other applications are contemplated.

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

What is claimed is:

1. A method comprising:
    accessing signal data indicative of brain activity of a subject, wherein the signal data was collected by a noninvasive sensor comprising at least one electrode over a time period, wherein the time period includes one or more epochs;
    generating, based on the signal data, spectrogram data comprising:
        for each frequency band of a set of frequency bands of the spectrogram data, a power estimated at the frequency band for each epoch of the one or more epochs;
    identifying, based on the spectrogram data, a spectral signature of a particular frequency band of the set of frequency bands, wherein the spectral signature identifies a fluctuation of a relative amount of the power estimated across the one or more epochs;
    estimating that, the spectral signature is consistent with an indication that one or more physical movements of the subject have occurred during the one or more epochs;
    generating, based on the estimation, an output that predicts an attribute of a sequence of predicted sleep stages over the time period; and
    determining that the output is consistent with a classification of pathological condition of the subject, wherein the determination is based on comparing the output to one or more reference attributes indicative of sleep stages associated with other subjects with known classifications of the pathological condition, wherein the pathological condition includes one of epilepsy, Alzheimer's disease, Parkinson's disease, depression, brain trauma, insomnia, restless leg syndrome, or sleep apnea.

2. The method of claim 1, wherein the at least one electrode includes a dry electrode.

3. The method of claim 1, wherein the at least one electrode includes a wet electrode.

4. The method of claim 1, wherein the signal data is accessed from a single channel of an electroencephalogram (EEG).

5. The method of claim 1, wherein the predicted sleep stages of the subject include a Rapid Eye Movement (REM) sleep, wherein the spectral signature further identifies a presence of a bimodal distribution of the relative amount of the power estimated across the one or more epochs, and wherein the presence of the bimodal distribution is predictive of the REM sleep of the subject.

6. The method of claim 5, further comprising selecting a particular portion of the bimodal distribution predictive of the REM sleep of the subject, wherein the estimation that the one or more physical movements of the subject have occurred is further based on the particular portion of the bimodal distribution.

7. The method of claim 5, wherein the output includes another prediction identifying a sub-stage of the REM sleep of the subject.

8. The method of claim 1, wherein generating the spectrogram data further comprises:
    normalizing the spectrogram data by processing the spectrogram data using a normalization function, wherein the normalization function is configured to:
        for each frequency band of the set of frequency bands:
            generate a normalization parameter based on powers in the spectrogram data for the frequency band for each epoch of the one or more epochs; and
            normalize the powers of the frequency band in the spectrogram using the normalization parameter.

9. The method of claim 1, wherein identifying the spectral signature further comprises performing an independent or principal component analysis on the spectrogram data.

10. The method of claim 1, wherein the predicted sleep stages include an awake state of the subject.

11. The method of claim 1, wherein the output includes another prediction corresponding to a drug consumption, reaction, or dosage state of the subject, and wherein the drug consumption, reaction, or the dosage state is associated with a drug selected from a group consisting of steroids, theophylline, decongestants, benzodiazepines, antidepressants, monoamine oxidase inhibitors, selective serotonin reuptake inhibitors, thyroxine, oral contraceptive pills, antihypertensives, antihistamines, neuroleptics, amphetamines, barbiturates, and anesthetics.

12. The method of claim 1, wherein the predicted sleep stages include a Rapid Eye Movement (REM) sleep state and a Slow Wave Sleep (SWS) sleep state.

13. The method of claim 1, further comprising:
    determining, based on the classification of the pathological condition, a treatment for the subject, wherein administration of the treatment affects a particular sleep stage of the predicted sleep stages of the subject.

14. The method of claim 13, wherein the particular sleep stage is a Rapid Eye Movement (REM) sleep, wherein the pathological condition is Alzheimer's disease, and wherein the treatment includes cholinesterase inhibitors that affect the REM sleep.

15. The method of claim 13, wherein the particular sleep stage is a Rapid Eye Movement (REM) sleep, wherein the pathological condition is depression, and wherein the treatment includes Monoamine oxidase inhibitors (MAOIs) that affect the REM sleep.

16. An apparatus comprising:
    a noninvasive sensor comprising at least one electrode; and
    a computing device, wherein the at least one electrode of the noninvasive sensor is in operable connection to the computing device, the computing device comprising one or more data processors and a non-transitory computer readable storage medium containing instructions which, when executed on the one or more data processors, cause the one or more data processors to perform actions including:
accessing signal data indicative of brain activity of a subject, wherein the signal data was collected by the noninvasive sensor over a time period, wherein the time period includes one or more epochs;
generating, based on the signal data, spectrogram data comprising:
for each frequency band of a set of frequency bands of the spectrogram data, a power estimated at the frequency band for each epoch of the one or more epochs;
identifying, based on the spectrogram data, a spectral signature of a particular frequency band of the set of frequency bands, wherein the spectral signature identifies a fluctuation of a relative amount of the power estimated across the one or more epochs;
estimating that the spectral signature is consistent with an indication that one or more physical movements of the subject have occurred during the one or more epochs;
generating, based on the estimation, an output that predicts an attribute of a sequence of predicted sleep stages over the time period; and
determining that the output is consistent with a classification of pathological condition of the subject, wherein the determination is based on comparing the output to one or more reference attributes indicative of sleep stages associated with other subjects with known classifications of the pathological condition, wherein the pathological condition includes one of epilepsy, Alzheimer's disease, Parkinson's disease, depression, brain trauma, insomnia, restless leg syndrome, or sleep apnea.

17. The apparatus of claim 16, wherein the at least one electrode includes a dry electrode.

18. The apparatus of claim 16, wherein the signal data is accessed from at least a single channel of an electroencephalogram (EEG).

19. The apparatus of claim 16, wherein the predicted sleep stages of the subject include a Rapid Eye Movement (REM) sleep, wherein the spectral signature further identifies a presence of a bimodal distribution of the relative amount of the power estimated across the one or more epochs, and wherein the presence of the bimodal distribution is predictive of the REM sleep of the subject.

20. The apparatus of claim 19, wherein the instructions further cause the one or more data processors to perform actions including:
selecting a particular portion of the bimodal distribution predictive of the REM sleep of the subject, wherein the estimation that the one or more physical movements of the subject have occurred is further based on the particular portion of the bimodal distribution.

21. The apparatus of claim 16, wherein identifying the spectral signature further comprises performing an independent or principal component analysis on the spectrogram data.

22. The apparatus of claim 16, wherein the output includes another prediction corresponding to a drug consumption, reaction, or dosage state of the subject, and wherein the drug consumption, reaction, or the dosage state is associated with a drug selected from a group consisting of steroids, theophylline, decongestants, benzodiazepines, antidepressants, monoamine oxidase inhibitors, selective serotonin reuptake inhibitors, thyroxine, oral contraceptive pills, antihypertensives, antihistamines, neuroleptics, amphetamines, barbiturates, and anesthetics.

23. The apparatus of claim 16, wherein the predicted sleep stages include a Rapid Eye Movement (REM) sleep state and a Slow Wave Sleep (SWS) sleep state.

* * * * *

UNITED STATES PATENT AND TRADEMARK OFFICE
CERTIFICATE OF CORRECTION

| | | |
|---|---|---|
| PATENT NO. | : 11,696,724 B2 | Page 1 of 1 |
| APPLICATION NO. | : 16/442337 | |
| DATED | : July 11, 2023 | |
| INVENTOR(S) | : Low | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 282 days.

Signed and Sealed this
Eighth Day of July, 2025

Coke Morgan Stewart
*Acting Director of the United States Patent and Trademark Office*